(12) United States Patent
Widenhouse et al.

(10) Patent No.: US 9,089,330 B2
(45) Date of Patent: Jul. 28, 2015

(54) SURGICAL BOWEL RETRACTOR DEVICES

(75) Inventors: Tamara Widenhouse, Clarksville, OH (US); Andrew Yoo, Cincinnati, OH (US); Frederick E. Shelton, IV, Hillsboro, OH (US); Katherine J. Schmid, Cincinnati, OH (US); Aron O. Zingman, Cambridge, MA (US); Richard W. Timm, Cincinnati, OH (US); Jacob S. Gee, Cincinnati, OH (US); Steven G. Hall, Cincinnati, OH (US); Daniel J. Mumaw, Johannesburg (ZA); Taylor W. Aronhalt, Loveland, OH (US); Gregory W. Johnson, Milford, OH (US); Michael J. Vendely, Lebanon, OH (US); Andrew T. Beckman, Cincinnati, OH (US); James R. Janszen, Cleves, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 228 days.

(21) Appl. No.: 13/181,827

(22) Filed: Jul. 13, 2011

(65) Prior Publication Data

US 2012/0238824 A1    Sep. 20, 2012

Related U.S. Application Data

(60) Provisional application No. 61/452,432, filed on Mar. 14, 2011.

(51) Int. Cl.
*A61B 17/02* (2006.01)
*A61B 17/115* (2006.01)
*A61B 17/34* (2006.01)
(Continued)

(52) U.S. Cl.
CPC ....... *A61B 17/1155* (2013.01); *A61B 17/00234* (2013.01); *A61B 17/3417* (2013.01); *A61B 2017/00287* (2013.01); *A61B 2017/00477* (2013.01); *A61B 2017/07257* (2013.01)

(58) Field of Classification Search
CPC .................. A61B 17/02; A61B 2017/0225
USPC ................................... 600/201–246
See application file for complete search history.

(56) References Cited

U.S. PATENT DOCUMENTS 2,224,882 A    12/1940    Peck
2,742,955 A    4/1956    Dominguez
(Continued)

FOREIGN PATENT DOCUMENTS

CA    2458946 A1    3/2003
CA    2512960 A1    1/2006
(Continued)

OTHER PUBLICATIONS

Definition of "interwoven", [online], [retrieved Feb. 14, 2013], retrieved from the Internet <URL:http://www.collinsdictionary.com/dictionary/english/interwoven>.*

(Continued)

*Primary Examiner* — Jerry Cumberledge

(57) ABSTRACT

Bowel retractor devices. In various forms, the bowel retractor devices are configurable from a collapsed position wherein the retractor may be inserted through a trocar cannula or other opening in a patient's body to a second expanded position wherein at least a portion of the patient's bowel may be advantageously supported in a desired position.

6 Claims, 22 Drawing Sheets

(51) Int. Cl.
  *A61B 17/00* (2006.01)
  *A61B 17/072* (2006.01)

(56) References Cited

U.S. PATENT DOCUMENTS

| | | | |
|---|---|---|---|
| 3,166,072 A | 1/1965 | Sullivan, Jr. | |
| 3,863,639 A * | 2/1975 | Kleaveland | 128/850 |
| 4,190,042 A | 2/1980 | Sinnreich | |
| 4,274,398 A * | 6/1981 | Scott, Jr. | 600/233 |
| 4,505,272 A | 3/1985 | Utyamyshev et al. | |
| 4,505,414 A | 3/1985 | Filipi | |
| 4,654,028 A | 3/1987 | Suma | |
| 4,700,703 A | 10/1987 | Resnick et al. | |
| 4,744,363 A | 5/1988 | Hasson | |
| 4,873,977 A | 10/1989 | Avant et al. | |
| 4,893,622 A | 1/1990 | Green et al. | |
| 4,903,697 A | 2/1990 | Resnick et al. | |
| 4,909,789 A | 3/1990 | Taguchi et al. | |
| 4,984,564 A * | 1/1991 | Yuen | 600/207 |
| 5,071,430 A | 12/1991 | de Salis et al. | |
| 5,104,025 A | 4/1992 | Main et al. | |
| 5,122,156 A | 6/1992 | Granger et al. | |
| 5,139,513 A | 8/1992 | Segato | |
| 5,158,567 A | 10/1992 | Green | |
| 5,195,505 A | 3/1993 | Josefsen | |
| 5,197,649 A | 3/1993 | Bessler et al. | |
| 5,205,459 A | 4/1993 | Brinkerhoff et al. | |
| 5,211,655 A | 5/1993 | Hasson | |
| 5,222,963 A | 6/1993 | Brinkerhoff et al. | |
| 5,222,975 A | 6/1993 | Crainich | |
| 5,234,447 A | 8/1993 | Kaster et al. | |
| 5,236,440 A | 8/1993 | Hlavacek | |
| 5,258,009 A | 11/1993 | Conners | |
| 5,282,829 A | 2/1994 | Hermes | |
| 5,285,945 A | 2/1994 | Brinkerhoff et al. | |
| 5,304,204 A | 4/1994 | Bregen | |
| 5,309,927 A | 5/1994 | Welch | |
| 5,336,232 A | 8/1994 | Green et al. | |
| 5,342,385 A * | 8/1994 | Norelli et al. | 606/193 |
| 5,342,395 A | 8/1994 | Jarrett et al. | |
| 5,342,396 A | 8/1994 | Cook | |
| 5,350,400 A | 9/1994 | Esposito et al. | |
| 5,354,250 A | 10/1994 | Christensen | |
| 5,366,479 A | 11/1994 | McGarry et al. | |
| 5,375,588 A | 12/1994 | Yoon | |
| 5,395,030 A | 3/1995 | Kuramoto et al. | |
| 5,404,870 A | 4/1995 | Brinkerhoff et al. | |
| 5,405,360 A * | 4/1995 | Tovey | 606/151 |
| 5,411,508 A | 5/1995 | Bessler et al. | |
| 5,425,745 A | 6/1995 | Green et al. | |
| 5,445,644 A | 8/1995 | Pietrafitta et al. | |
| 5,474,057 A | 12/1995 | Makower et al. | |
| 5,478,354 A | 12/1995 | Tovey et al. | |
| 5,503,635 A | 4/1996 | Sauer et al. | |
| 5,520,609 A * | 5/1996 | Moll et al. | 600/204 |
| 5,527,264 A * | 6/1996 | Moll et al. | 600/204 |
| 5,531,856 A * | 7/1996 | Moll et al. | 156/290 |
| 5,549,621 A | 8/1996 | Bessler et al. | |
| 5,554,169 A | 9/1996 | Green et al. | |
| 5,562,690 A | 10/1996 | Green et al. | |
| 5,571,285 A | 11/1996 | Chow et al. | |
| 5,575,803 A | 11/1996 | Cooper et al. | |
| 5,613,937 A * | 3/1997 | Garrison et al. | 600/201 |
| 5,618,307 A | 4/1997 | Donlon et al. | |
| 5,620,452 A | 4/1997 | Yoon | |
| 5,651,762 A * | 7/1997 | Bridges | 600/210 |
| 5,653,721 A | 8/1997 | Knodel et al. | |
| 5,667,517 A | 9/1997 | Hooven | |
| 5,667,527 A | 9/1997 | Cook | |
| 5,681,341 A * | 10/1997 | Lunsford et al. | 606/192 |
| 5,683,349 A | 11/1997 | Makower et al. | |
| 5,695,504 A | 12/1997 | Gifford, III et al. | |
| 5,695,524 A | 12/1997 | Kelley et al. | |
| 5,697,943 A | 12/1997 | Sauer et al. | |
| 5,702,409 A | 12/1997 | Rayburn et al. | |
| 5,725,554 A | 3/1998 | Simon et al. | |
| 5,730,758 A | 3/1998 | Allgeyer | |
| 5,738,629 A * | 4/1998 | Moll et al. | 600/116 |
| 5,752,965 A | 5/1998 | Francis et al. | |
| 5,766,188 A | 6/1998 | Igaki | |
| 5,769,892 A | 6/1998 | Kingwell | |
| 5,810,721 A * | 9/1998 | Mueller et al. | 600/206 |
| 5,810,855 A | 9/1998 | Rayburn et al. | |
| 5,814,057 A | 9/1998 | Oi et al. | |
| 5,839,369 A | 11/1998 | Chatterjee et al. | |
| 5,839,639 A | 11/1998 | Sauer et al. | |
| 5,860,581 A | 1/1999 | Robertson et al. | |
| 5,906,577 A | 5/1999 | Beane et al. | |
| 5,964,774 A | 10/1999 | McKean et al. | |
| 6,024,748 A | 2/2000 | Manzo et al. | |
| 6,063,025 A * | 5/2000 | Bridges et al. | 600/208 |
| 6,063,097 A | 5/2000 | Oi et al. | |
| 6,083,234 A | 7/2000 | Nicholas et al. | |
| 6,083,242 A | 7/2000 | Cook | |
| 6,099,551 A | 8/2000 | Gabbay | |
| 6,142,933 A | 11/2000 | Longo et al. | |
| 6,171,330 B1 | 1/2001 | Benchetrit | |
| 6,221,007 B1 | 4/2001 | Green | |
| 6,248,117 B1 | 6/2001 | Blatter | |
| 6,254,534 B1 | 7/2001 | Butler et al. | |
| 6,258,107 B1 | 7/2001 | Balázs et al. | |
| 6,325,810 B1 | 12/2001 | Hamilton et al. | |
| 6,338,737 B1 | 1/2002 | Toledano | |
| 6,346,077 B1 | 2/2002 | Taylor et al. | |
| 6,352,503 B1 | 3/2002 | Matsui et al. | |
| 6,387,113 B1 | 5/2002 | Hawkins et al. | |
| 6,391,038 B2 | 5/2002 | Vargas et al. | |
| 6,398,797 B2 | 6/2002 | Bombard et al. | |
| 6,402,766 B2 | 6/2002 | Bowman et al. | |
| RE37,814 E | 8/2002 | Allgeyer | |
| 6,436,110 B2 | 8/2002 | Bowman et al. | |
| 6,440,146 B2 | 8/2002 | Nicholas et al. | |
| 6,443,973 B1 | 9/2002 | Whitman | |
| 6,447,523 B1 * | 9/2002 | Middleman et al. | 606/127 |
| 6,458,077 B1 | 10/2002 | Boebel et al. | |
| 6,494,885 B1 | 12/2002 | Dhindsa | |
| 6,503,257 B2 | 1/2003 | Grant et al. | |
| 6,503,259 B2 | 1/2003 | Huxel et al. | |
| 6,517,565 B1 | 2/2003 | Whitman et al. | |
| 6,517,566 B1 | 2/2003 | Hovland et al. | |
| 6,551,333 B2 | 4/2003 | Kuhns et al. | |
| 6,592,597 B2 | 7/2003 | Grant et al. | |
| 6,616,686 B2 | 9/2003 | Coleman et al. | |
| 6,629,988 B2 | 10/2003 | Weadock | |
| 6,638,285 B2 | 10/2003 | Gabbay | |
| 6,638,297 B1 | 10/2003 | Huitema | |
| 6,645,201 B1 | 11/2003 | Utley et al. | |
| 6,656,193 B2 | 12/2003 | Grant et al. | |
| 6,692,507 B2 | 2/2004 | Pugsley et al. | |
| 6,716,233 B1 | 4/2004 | Whitman | |
| 6,726,697 B2 | 4/2004 | Nicholas et al. | |
| 6,736,825 B2 | 5/2004 | Blatter et al. | |
| 6,769,590 B2 | 8/2004 | Vresh et al. | |
| 6,821,284 B2 | 11/2004 | Sturtz et al. | |
| 6,846,307 B2 | 1/2005 | Whitman et al. | |
| 6,872,214 B2 | 3/2005 | Sonnenschein et al. | |
| 6,913,608 B2 | 7/2005 | Liddicoat et al. | |
| 6,939,358 B2 | 9/2005 | Palacios et al. | |
| 6,960,220 B2 | 11/2005 | Marino et al. | |
| 6,981,978 B2 | 1/2006 | Gannoe | |
| 7,052,454 B2 * | 5/2006 | Taylor | 600/114 |
| 7,056,330 B2 | 6/2006 | Gayton | |
| 7,063,712 B2 | 6/2006 | Vargas et al. | |
| 7,066,944 B2 | 6/2006 | Laufer et al. | |
| 7,077,856 B2 | 7/2006 | Whitman | |
| 7,080,769 B2 | 7/2006 | Vresh et al. | |
| 7,083,626 B2 | 8/2006 | Hart et al. | |
| 7,108,701 B2 | 9/2006 | Evens et al. | |
| 7,108,709 B2 | 9/2006 | Cummins | |
| 7,128,748 B2 | 10/2006 | Mooradian et al. | |
| 7,156,863 B2 | 1/2007 | Sonnenschein et al. | |
| 7,179,267 B2 | 2/2007 | Nolan et al. | |
| 7,220,272 B2 | 5/2007 | Weadock | |
| 7,238,195 B2 | 7/2007 | Viola | |

(56) References Cited

U.S. PATENT DOCUMENTS

| | | | | |
|---|---|---|---|---|
| 7,267,679 | B2 | 9/2007 | McGuckin, Jr. et al. | |
| 7,328,828 | B2 | 2/2008 | Ortiz et al. | |
| 7,338,505 | B2 | 3/2008 | Belson | |
| 7,354,447 | B2 | 4/2008 | Shelton, IV et al. | |
| 7,377,928 | B2 | 5/2008 | Zubik et al. | |
| 7,407,078 | B2 | 8/2008 | Shelton, IV et al. | |
| 7,416,101 | B2 | 8/2008 | Shelton, IV et al. | |
| 7,422,139 | B2 | 9/2008 | Shelton, IV et al. | |
| 7,431,189 | B2 | 10/2008 | Shelton, IV et al. | |
| 7,431,730 | B2 | 10/2008 | Viola | |
| 7,434,717 | B2 | 10/2008 | Shelton, IV et al. | |
| 7,438,209 | B1 | 10/2008 | Hess et al. | |
| 7,441,684 | B2 | 10/2008 | Shelton, IV et al. | |
| 7,441,685 | B1 | 10/2008 | Boudreaux | |
| 7,448,525 | B2 | 11/2008 | Shelton, IV et al. | |
| 7,455,682 | B2 | 11/2008 | Viola | |
| 7,464,846 | B2 | 12/2008 | Shelton, IV et al. | |
| 7,464,849 | B2 | 12/2008 | Shelton, IV et al. | |
| 7,467,740 | B2 | 12/2008 | Shelton, IV et al. | |
| 7,472,815 | B2 | 1/2009 | Shelton, IV et al. | |
| 7,473,221 | B2* | 1/2009 | Ewers et al. | 600/208 |
| 7,490,749 | B2 | 2/2009 | Schall et al. | |
| 7,491,232 | B2 | 2/2009 | Bolduc et al. | |
| 7,500,979 | B2 | 3/2009 | Hueil et al. | |
| 7,506,791 | B2 | 3/2009 | Omaits et al. | |
| 7,510,107 | B2 | 3/2009 | Timm et al. | |
| 7,517,356 | B2 | 4/2009 | Heinrich | |
| 7,547,312 | B2 | 6/2009 | Bauman et al. | |
| 7,549,564 | B2 | 6/2009 | Boudreaux | |
| 7,568,603 | B2 | 8/2009 | Shelton, IV et al. | |
| 7,588,175 | B2 | 9/2009 | Timm et al. | |
| 7,588,176 | B2 | 9/2009 | Timm et al. | |
| 7,597,229 | B2 | 10/2009 | Boudreaux et al. | |
| 7,604,150 | B2 | 10/2009 | Boudreaux | |
| 7,604,151 | B2 | 10/2009 | Hess et al. | |
| 7,607,557 | B2 | 10/2009 | Shelton, IV et al. | |
| 7,644,848 | B2 | 1/2010 | Swayze et al. | |
| 7,658,311 | B2 | 2/2010 | Boudreaux | |
| 7,665,647 | B2 | 2/2010 | Shelton, IV et al. | |
| 7,669,746 | B2 | 3/2010 | Shelton, IV | |
| 7,669,747 | B2 | 3/2010 | Weisenburgh, II et al. | |
| 7,670,334 | B2 | 3/2010 | Hueil et al. | |
| 7,673,780 | B2 | 3/2010 | Shelton, IV et al. | |
| 7,673,781 | B2 | 3/2010 | Swayze et al. | |
| 7,673,782 | B2 | 3/2010 | Hess et al. | |
| 7,673,783 | B2 | 3/2010 | Morgan et al. | |
| 7,682,686 | B2* | 3/2010 | Curro et al. | 428/172 |
| 7,686,201 | B2 | 3/2010 | Csiky | |
| 7,699,844 | B2 | 4/2010 | Utley et al. | |
| 7,699,859 | B2 | 4/2010 | Bombard et al. | |
| 7,708,181 | B2 | 5/2010 | Cole et al. | |
| 7,721,931 | B2 | 5/2010 | Shelton, IV et al. | |
| 7,721,934 | B2 | 5/2010 | Shelton, IV et al. | |
| 7,721,936 | B2 | 5/2010 | Shalton, IV et al. | |
| 7,731,072 | B2 | 6/2010 | Timm et al. | |
| 7,735,703 | B2 | 6/2010 | Morgan et al. | |
| 7,738,971 | B2 | 6/2010 | Swayze et al. | |
| 7,740,159 | B2 | 6/2010 | Shelton, IV et al. | |
| 7,753,245 | B2 | 7/2010 | Boudreaux et al. | |
| 7,753,904 | B2 | 7/2010 | Shelton, IV et al. | |
| 7,766,209 | B2 | 8/2010 | Baxter, III et al. | |
| 7,766,210 | B2 | 8/2010 | Shelton, IV et al. | |
| 7,770,775 | B2 | 8/2010 | Shelton, IV et al. | |
| 7,776,060 | B2 | 8/2010 | Mooradian et al. | |
| 7,780,685 | B2 | 8/2010 | Hunt et al. | |
| 7,793,812 | B2 | 9/2010 | Moore et al. | |
| 7,794,475 | B2 | 9/2010 | Hess et al. | |
| 7,798,386 | B2 | 9/2010 | Schall et al. | |
| 7,799,039 | B2 | 9/2010 | Shelton, IV et al. | |
| 7,810,692 | B2 | 10/2010 | Hall et al. | |
| 7,810,693 | B2 | 10/2010 | Broehl et al. | |
| 7,819,296 | B2 | 10/2010 | Hueil et al. | |
| 7,819,297 | B2 | 10/2010 | Doll et al. | |
| 7,819,298 | B2 | 10/2010 | Hall et al. | |
| 7,819,299 | B2 | 10/2010 | Shelton, IV et al. | |
| 7,832,408 | B2 | 11/2010 | Shelton, IV et al. | |
| 7,832,612 | B2 | 11/2010 | Baxter, III et al. | |
| 7,837,080 | B2 | 11/2010 | Schwemberger | |
| 7,845,537 | B2 | 12/2010 | Shelton, IV et al. | |
| 7,857,185 | B2 | 12/2010 | Swayze et al. | |
| 7,857,186 | B2 | 12/2010 | Baxter, III et al. | |
| 7,861,906 | B2 | 1/2011 | Doll et al. | |
| 7,862,502 | B2* | 1/2011 | Pool et al. | 600/37 |
| 7,866,527 | B2 | 1/2011 | Hall et al. | |
| 7,871,418 | B2 | 1/2011 | Thompson et al. | |
| 7,900,805 | B2 | 3/2011 | Shelton, IV et al. | |
| 7,905,380 | B2 | 3/2011 | Shelton, IV et al. | |
| 7,905,381 | B2 | 3/2011 | Baxter, III et al. | |
| 7,913,891 | B2 | 3/2011 | Doll et al. | |
| 7,914,543 | B2 | 3/2011 | Roth et al. | |
| 7,918,377 | B2 | 4/2011 | Measamer et al. | |
| 7,922,061 | B2 | 4/2011 | Shelton, IV et al. | |
| 7,934,630 | B2 | 5/2011 | Shelton, IV et al. | |
| 7,942,890 | B2 | 5/2011 | D'Agostino et al. | |
| 7,954,682 | B2 | 6/2011 | Giordano et al. | |
| 7,954,684 | B2 | 6/2011 | Boudreaux | |
| 7,954,686 | B2 | 6/2011 | Baxter, III et al. | |
| 7,955,253 | B2 | 6/2011 | Ewers et al. | |
| 7,959,051 | B2 | 6/2011 | Smith et al. | |
| 7,966,799 | B2 | 6/2011 | Morgan et al. | |
| 7,967,791 | B2 | 6/2011 | Franer et al. | |
| 7,980,443 | B2 | 7/2011 | Scheib et al. | |
| 8,002,696 | B2 | 8/2011 | Suzuki | |
| 8,002,795 | B2 | 8/2011 | Beetel | |
| 8,020,743 | B2 | 9/2011 | Shelton, IV | |
| 8,034,077 | B2 | 10/2011 | Smith et al. | |
| 8,056,787 | B2 | 11/2011 | Boudreaux et al. | |
| 8,066,167 | B2 | 11/2011 | Measamer et al. | |
| D650,074 | S | 12/2011 | Hunt et al. | |
| 8,075,476 | B2 | 12/2011 | Vargas | |
| 8,083,120 | B2 | 12/2011 | Shelton, IV et al. | |
| 8,097,017 | B2 | 1/2012 | Viola | |
| 8,113,410 | B2 | 2/2012 | Hall et al. | |
| 8,123,767 | B2 | 2/2012 | Bauman et al. | |
| 8,128,645 | B2 | 3/2012 | Sonnenschein et al. | |
| 8,136,712 | B2 | 3/2012 | Zingman | |
| 8,141,762 | B2 | 3/2012 | Bedi et al. | |
| 8,157,145 | B2 | 4/2012 | Shelton, IV et al. | |
| 8,157,153 | B2 | 4/2012 | Shelton, IV et al. | |
| 8,161,977 | B2 | 4/2012 | Shelton, IV et al. | |
| 8,167,185 | B2 | 5/2012 | Shelton, IV et al. | |
| 8,172,124 | B2 | 5/2012 | Shelton, IV et al. | |
| 8,186,555 | B2 | 5/2012 | Shelton, IV et al. | |
| 8,186,560 | B2 | 5/2012 | Hess et al. | |
| 8,196,795 | B2 | 6/2012 | Moore et al. | |
| 8,196,796 | B2 | 6/2012 | Shelton, IV et al. | |
| 8,205,781 | B2 | 6/2012 | Baxter, III et al. | |
| 8,210,411 | B2 | 7/2012 | Yates et al. | |
| 8,211,125 | B2 | 7/2012 | Spivey | |
| 8,215,531 | B2 | 7/2012 | Shelton, IV et al. | |
| 8,226,553 | B2 | 7/2012 | Shelton, IV et al. | |
| 8,257,251 | B2 | 9/2012 | Shelton, IV et al. | |
| 8,267,300 | B2 | 9/2012 | Boudreaux | |
| 8,292,155 | B2 | 10/2012 | Shelton, IV et al. | |
| 8,308,040 | B2 | 11/2012 | Huang et al. | |
| 8,317,070 | B2 | 11/2012 | Hueil et al. | |
| 8,322,455 | B2 | 12/2012 | Shelton, IV et al. | |
| 8,322,589 | B2 | 12/2012 | Boudreaux | |
| 8,333,313 | B2 | 12/2012 | Boudreaux et al. | |
| 8,348,129 | B2 | 1/2013 | Bedi et al. | |
| 8,348,131 | B2 | 1/2013 | Omaits et al. | |
| 8,348,837 | B2 | 1/2013 | Wenchell | |
| 8,353,437 | B2 | 1/2013 | Boudreaux | |
| 8,353,438 | B2 | 1/2013 | Baxter, III et al. | |
| 8,353,439 | B2 | 1/2013 | Baxter, III et al. | |
| 8,372,094 | B2 | 2/2013 | Bettuchi et al. | |
| 8,398,669 | B2 | 3/2013 | Kim | |
| 8,485,970 | B2 | 7/2013 | Widenhouse et al. | |
| 8,579,937 | B2 | 11/2013 | Gresham | |
| 8,727,961 | B2* | 5/2014 | Ziv | 600/29 |
| 8,758,235 | B2* | 6/2014 | Jaworek | 600/206 |
| 2002/0010389 | A1* | 1/2002 | Butler et al. | 600/208 |
| 2003/0190584 | A1* | 10/2003 | Heasley | 433/136 |
| 2003/0220660 | A1 | 11/2003 | Kortenbach et al. | |

(56) References Cited

U.S. PATENT DOCUMENTS

| | | |
|---|---|---|
| 2004/0006372 A1 | 1/2004 | Racenet et al. |
| 2004/0097987 A1 | 5/2004 | Pugsley et al. |
| 2004/0158261 A1 | 8/2004 | Vu |
| 2004/0167572 A1 | 8/2004 | Roth et al. |
| 2004/0193189 A1 | 9/2004 | Kortenbach et al. |
| 2004/0254608 A1 | 12/2004 | Huitema et al. |
| 2004/0260315 A1 | 12/2004 | Dell et al. |
| 2004/0267310 A1 | 12/2004 | Racenet et al. |
| 2005/0059997 A1 | 3/2005 | Bauman et al. |
| 2005/0070929 A1 | 3/2005 | Dalessandro et al. |
| 2005/0177181 A1 | 8/2005 | Kagan et al. |
| 2005/0187576 A1 | 8/2005 | Whitman et al. |
| 2005/0192628 A1 | 9/2005 | Viola |
| 2005/0203550 A1 | 9/2005 | Laufer et al. |
| 2005/0216055 A1 | 9/2005 | Scirica et al. |
| 2005/0240222 A1 | 10/2005 | Shipp |
| 2005/0283188 A1* | 12/2005 | Loshakove et al. ............ 606/213 |
| 2006/0004261 A1* | 1/2006 | Douglas ......................... 600/210 |
| 2006/0047307 A1 | 3/2006 | Ortiz et al. |
| 2006/0052825 A1 | 3/2006 | Ransick et al. |
| 2006/0085033 A1 | 4/2006 | Criscuolo et al. |
| 2006/0161050 A1 | 7/2006 | Butler et al. |
| 2006/0161185 A1 | 7/2006 | Saadat et al. |
| 2006/0173470 A1 | 8/2006 | Oray et al. |
| 2006/0201989 A1 | 9/2006 | Ojeda |
| 2006/0235469 A1 | 10/2006 | Viola |
| 2006/0241692 A1 | 10/2006 | McGuckin, Jr. et al. |
| 2006/0252993 A1 | 11/2006 | Freed et al. |
| 2007/0043387 A1 | 2/2007 | Vargas et al. |
| 2007/0073341 A1 | 3/2007 | Smith |
| 2007/0088241 A1* | 4/2007 | Brustad et al. ................... 602/60 |
| 2007/0102472 A1 | 5/2007 | Shelton, IV |
| 2007/0106317 A1 | 5/2007 | Shelton, IV et al. |
| 2007/0118175 A1* | 5/2007 | Butler et al. ................... 606/213 |
| 2007/0156023 A1* | 7/2007 | Frasier et al. ................... 600/206 |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175955 A1 | 8/2007 | Shelton, IV et al. |
| 2007/0194079 A1 | 8/2007 | Hueil et al. |
| 2007/0194082 A1 | 8/2007 | Morgan et al. |
| 2007/0203510 A1 | 8/2007 | Bettuchi |
| 2007/0225562 A1 | 9/2007 | Spivey et al. |
| 2007/0239028 A1 | 10/2007 | Houser et al. |
| 2007/0276189 A1 | 11/2007 | Abel et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078807 A1 | 4/2008 | Hess et al. |
| 2008/0078808 A1 | 4/2008 | Hess et al. |
| 2008/0082114 A1 | 4/2008 | McKenna et al. |
| 2008/0082125 A1 | 4/2008 | Murray et al. |
| 2008/0140115 A1 | 6/2008 | Stopek |
| 2008/0154299 A1 | 6/2008 | Livneh |
| 2008/0167522 A1 | 7/2008 | Giordano et al. |
| 2008/0167672 A1 | 7/2008 | Giordano et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0172088 A1 | 7/2008 | Smith et al. |
| 2008/0200933 A1 | 8/2008 | Bakos et al. |
| 2008/0242939 A1 | 10/2008 | Johnston |
| 2008/0255519 A1 | 10/2008 | Piskun et al. |
| 2008/0294179 A1 | 11/2008 | Balbierz et al. |
| 2008/0296346 A1 | 12/2008 | Shelton, IV et al. |
| 2008/0308602 A1 | 12/2008 | Timm et al. |
| 2008/0308603 A1 | 12/2008 | Shelton, IV et al. |
| 2009/0001121 A1 | 1/2009 | Hess et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0062618 A1* | 3/2009 | Drew et al. ................... 600/204 |
| 2009/0149871 A9 | 6/2009 | Kagan et al. |
| 2009/0157087 A1* | 6/2009 | Wei et al. ......................... 606/99 |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0209946 A1 | 8/2009 | Swayze et al. |
| 2009/0209979 A1 | 8/2009 | Yates et al. |
| 2009/0209990 A1 | 8/2009 | Yates et al. |
| 2009/0242610 A1 | 10/2009 | Shelton, IV et al. |
| 2009/0292176 A1* | 11/2009 | Bonadio et al. ............... 600/203 |
| 2010/0069942 A1 | 3/2010 | Shelton, IV |
| 2010/0076475 A1 | 3/2010 | Yates et al. |
| 2010/0087840 A1 | 4/2010 | Ebersole et al. |
| 2010/0089970 A1 | 4/2010 | Smith et al. |
| 2010/0127042 A1 | 5/2010 | Shelton, IV |
| 2010/0133317 A1 | 6/2010 | Shelton, IV et al. |
| 2010/0179382 A1 | 7/2010 | Shelton, IV et al. |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0213241 A1 | 8/2010 | Bedi et al. |
| 2010/0222901 A1 | 9/2010 | Swayze et al. |
| 2010/0224669 A1 | 9/2010 | Shelton, IV et al. |
| 2010/0228091 A1 | 9/2010 | Widenhouse et al. |
| 2010/0243709 A1 | 9/2010 | Hess et al. |
| 2010/0264193 A1 | 10/2010 | Huang et al. |
| 2010/0292540 A1* | 11/2010 | Hess et al. ................... 600/206 |
| 2010/0294829 A1 | 11/2010 | Giordano et al. |
| 2010/0301095 A1 | 12/2010 | Shelton, IV et al. |
| 2010/0305408 A1* | 12/2010 | Albrecht et al. ............... 600/208 |
| 2010/0305552 A1 | 12/2010 | Shelton, IV et al. |
| 2010/0312261 A1 | 12/2010 | Suzuki et al. |
| 2010/0331880 A1 | 12/2010 | Stopek |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0024477 A1 | 2/2011 | Hall et al. |
| 2011/0024478 A1 | 2/2011 | Shelton, IV |
| 2011/0024479 A1 | 2/2011 | Swensgard et al. |
| 2011/0042441 A1 | 2/2011 | Shelton, IV et al. |
| 2011/0060363 A1 | 3/2011 | Hess et al. |
| 2011/0068145 A1 | 3/2011 | Bedi et al. |
| 2011/0068148 A1 | 3/2011 | Hall et al. |
| 2011/0087276 A1 | 4/2011 | Bedi et al. |
| 2011/0087279 A1 | 4/2011 | Shah et al. |
| 2011/0114697 A1 | 5/2011 | Baxter, III et al. |
| 2011/0114700 A1 | 5/2011 | Baxter, III et al. |
| 2011/0118761 A1 | 5/2011 | Baxter, III et al. |
| 2011/0125176 A1 | 5/2011 | Yates et al. |
| 2011/0125177 A1 | 5/2011 | Yates et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0144430 A1 | 6/2011 | Spivey et al. |
| 2011/0147433 A1 | 6/2011 | Shelton, IV et al. |
| 2011/0147434 A1 | 6/2011 | Hueil et al. |
| 2011/0155781 A1 | 6/2011 | Swensgard et al. |
| 2011/0155785 A1 | 6/2011 | Laurent et al. |
| 2011/0155787 A1 | 6/2011 | Baxter, III et al. |

(56) References Cited

U.S. PATENT DOCUMENTS

| | | |
|---|---|---|
| 2011/0163147 A1 | 7/2011 | Laurent et al. |
| 2011/0172495 A1* | 7/2011 | Armstrong .................... 600/233 |
| 2011/0174861 A1 | 7/2011 | Shelton, IV et al. |
| 2011/0174863 A1 | 7/2011 | Shelton, IV et al. |
| 2011/0192882 A1 | 8/2011 | Hess et al. |
| 2011/0226837 A1 | 9/2011 | Baxter, III et al. |
| 2011/0275901 A1 | 11/2011 | Shelton, IV |
| 2011/0276083 A1 | 11/2011 | Shelton, IV et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2011/0295242 A1 | 12/2011 | Spivey et al. |
| 2011/0295269 A1 | 12/2011 | Swensgard et al. |
| 2011/0295270 A1 | 12/2011 | Giordano et al. |
| 2011/0295295 A1 | 12/2011 | Shelton, IV et al. |
| 2012/0024934 A1 | 2/2012 | Shelton, IV et al. |
| 2012/0024935 A1 | 2/2012 | Shelton, IV et al. |
| 2012/0024936 A1 | 2/2012 | Baxter, III et al. |
| 2012/0029272 A1 | 2/2012 | Shelton, IV et al. |
| 2012/0029544 A1 | 2/2012 | Shelton, IV et al. |
| 2012/0029547 A1 | 2/2012 | Shelton, IV et al. |
| 2012/0046692 A1 | 2/2012 | Smith et al. |
| 2012/0061448 A1 | 3/2012 | Zingman |
| 2012/0071711 A1 | 3/2012 | Shelton, IV et al. |
| 2012/0071866 A1 | 3/2012 | Kerr et al. |
| 2012/0074196 A1 | 3/2012 | Shelton, IV et al. |
| 2012/0074198 A1 | 3/2012 | Huitema et al. |
| 2012/0074200 A1 | 3/2012 | Schmid et al. |
| 2012/0074201 A1 | 3/2012 | Baxter, III et al. |
| 2012/0080332 A1 | 4/2012 | Shelton, IV et al. |
| 2012/0080333 A1 | 4/2012 | Woodard, Jr. et al. |
| 2012/0080334 A1 | 4/2012 | Shelton, IV et al. |
| 2012/0080335 A1 | 4/2012 | Shelton, IV et al. |
| 2012/0080336 A1 | 4/2012 | Shelton, IV et al. |
| 2012/0080337 A1 | 4/2012 | Shelton, IV et al. |
| 2012/0080338 A1 | 4/2012 | Shelton, IV et al. |
| 2012/0080339 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080345 A1 | 4/2012 | Morgan et al. |
| 2012/0080477 A1 | 4/2012 | Leimbach et al. |
| 2012/0080478 A1 | 4/2012 | Morgan et al. |
| 2012/0080479 A1 | 4/2012 | Shelton, IV |
| 2012/0080480 A1 | 4/2012 | Woodard, Jr. et al. |
| 2012/0080481 A1 | 4/2012 | Widenhouse et al. |
| 2012/0080482 A1 | 4/2012 | Schall et al. |
| 2012/0080483 A1 | 4/2012 | Riestenberg et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080487 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080496 A1 | 4/2012 | Schall et al. |
| 2012/0080498 A1 | 4/2012 | Shelton, IV et al. |
| 2012/0080499 A1 | 4/2012 | Schall et al. |
| 2012/0080500 A1 | 4/2012 | Morgan et al. |
| 2012/0080501 A1 | 4/2012 | Morgan et al. |
| 2012/0080502 A1 | 4/2012 | Morgan et al. |
| 2012/0080503 A1 | 4/2012 | Woodard, Jr. et al. |
| 2012/0083833 A1 | 4/2012 | Shelton, IV et al. |
| 2012/0083834 A1 | 4/2012 | Shelton, IV et al. |
| 2012/0083835 A1 | 4/2012 | Shelton, IV et al. |
| 2012/0083836 A1 | 4/2012 | Shelton, IV et al. |
| 2012/0132450 A1 | 5/2012 | Timm et al. |
| 2012/0138660 A1 | 6/2012 | Shelton, IV |
| 2012/0160721 A1 | 6/2012 | Shelton, IV et al. |
| 2012/0175399 A1 | 7/2012 | Shelton et al. |
| 2012/0199630 A1 | 8/2012 | Shelton, IV et al. |
| 2012/0199631 A1 | 8/2012 | Shelton, IV et al. |
| 2012/0199632 A1 | 8/2012 | Spivey et al. |
| 2012/0199633 A1 | 8/2012 | Shelton, IV et al. |
| 2012/0203247 A1 | 8/2012 | Shelton, IV et al. |
| 2012/0205421 A1 | 8/2012 | Shelton, IV |
| 2012/0211546 A1 | 8/2012 | Shelton, IV |
| 2012/0234890 A1 | 9/2012 | Aronhalt et al. |
| 2012/0234891 A1 | 9/2012 | Aronhalt et al. |
| 2012/0234892 A1 | 9/2012 | Aronhalt et al. |
| 2012/0234893 A1 | 9/2012 | Schuckmann et al. |
| 2012/0234895 A1 | 9/2012 | O'Connor et al. |
| 2012/0234896 A1 | 9/2012 | Ellerhorst et al. |
| 2012/0234897 A1 | 9/2012 | Shelton, IV et al. |
| 2012/0234898 A1 | 9/2012 | Shelton, IV et al. |
| 2012/0234899 A1 | 9/2012 | Scheib et al. |
| 2012/0234900 A1 | 9/2012 | Swayze |
| 2012/0238823 A1 | 9/2012 | Hagerty et al. |
| 2012/0238826 A1 | 9/2012 | Yoo et al. |
| 2012/0238829 A1 | 9/2012 | Shelton, IV et al. |
| 2012/0239009 A1 | 9/2012 | Mollere et al. |
| 2012/0239010 A1 | 9/2012 | Shelton, IV et al. |
| 2012/0239012 A1 | 9/2012 | Laurent et al. |
| 2012/0239075 A1 | 9/2012 | Widenhouse et al. |
| 2012/0239082 A1 | 9/2012 | Shelton, IV et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241505 A1 | 9/2012 | Alexander, III et al. |
| 2012/0248169 A1 | 10/2012 | Widenhouse et al. |
| 2012/0253298 A1 | 10/2012 | Henderson et al. |
| 2012/0265230 A1 | 10/2012 | Yates et al. |
| 2012/0273551 A1 | 11/2012 | Shelton, IV et al. |
| 2012/0283707 A1 | 11/2012 | Giordano et al. |
| 2012/0286019 A1 | 11/2012 | Hueil et al. |
| 2012/0292367 A1 | 11/2012 | Morgan et al. |
| 2012/0292370 A1 | 11/2012 | Hess et al. |
| 2012/0298719 A1 | 11/2012 | Shelton, IV et al. |
| 2013/0012931 A1 | 1/2013 | Spivey et al. |
| 2013/0012957 A1 | 1/2013 | Shelton, IV et al. |
| 2013/0018228 A1* | 1/2013 | Armstrong .................... 600/204 |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0041371 A1 | 2/2013 | Yates et al. |
| 2013/0105551 A1 | 5/2013 | Zingman |
| 2013/0317310 A1 | 11/2013 | Widenhouse et al. |

FOREIGN PATENT DOCUMENTS

| | | |
|---|---|---|
| CA | 2514274 A1 | 1/2006 |
| CN | 2488482 Y | 5/2002 |
| CN | 1634601 A | 7/2005 |
| CN | 1868411 A | 11/2006 |
| CN | 1915180 A | 2/2007 |
| CN | 101011286 A | 8/2007 |
| CN | 101095621 A | 1/2008 |
| DE | 273689 C | 5/1914 |
| DE | 1775926 A | 1/1972 |
| DE | 3036217 A1 | 4/1982 |
| DE | 3210466 A1 | 9/1983 |
| DE | 3709067 A1 | 9/1988 |
| DE | 9412228 U | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 20016423 U1 | 2/2001 |
| DE | 10052679 A1 | 5/2001 |
| DE | 20112837 U1 | 10/2001 |
| DE | 20121753 U1 | 4/2003 |

(56) References Cited

FOREIGN PATENT DOCUMENTS

| | | | |
|---|---|---|---|
| DE | 10314072 A1 | 10/2004 |
| DE | 202007003114 U1 | 6/2007 |
| EP | 0122046 A1 | 10/1984 |
| EP | 0070230 B1 | 10/1985 |
| EP | 0156774 A2 | 10/1985 |
| EP | 0387980 B1 | 10/1985 |
| EP | 0033548 B1 | 5/1986 |
| EP | 0129442 B1 | 11/1987 |
| EP | 0276104 A2 | 7/1988 |
| EP | 0178940 B1 | 1/1991 |
| EP | 0178941 B1 | 1/1991 |
| EP | 0248844 B1 | 1/1993 |
| EP | 0545029 A1 | 6/1993 |
| EP | 0277959 B1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0511470 B1 | 10/1995 |
| EP | 0674876 A2 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0705571 A1 | 4/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0843906 B1 | 3/2000 |
| EP | 0552050 B1 | 5/2000 |
| EP | 0833592 B1 | 5/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1090592 A1 | 4/2001 |
| EP | 1095627 A1 | 5/2001 |
| EP | 1256318 B1 | 5/2001 |
| EP | 0806914 B1 | 9/2001 |
| EP | 0768840 B1 | 12/2001 |
| EP | 0908152 B1 | 1/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 0717960 B1 | 2/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0741996 B1 | 2/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1459695 A1 | 9/2004 |
| EP | 1254636 B1 | 10/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1001710 B1 | 1/2005 |
| EP | 1520521 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1067876 B1 | 8/2005 |
| EP | 0870473 B1 | 9/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 1330989 B1 | 12/2005 |
| EP | 0771176 B2 | 1/2006 |
| EP | 1621138 A2 | 2/2006 |
| EP | 1621139 A2 | 2/2006 |
| EP | 1621141 A2 | 2/2006 |
| EP | 1621145 A2 | 2/2006 |
| EP | 1621151 A2 | 2/2006 |

(56) References Cited

FOREIGN PATENT DOCUMENTS

| | | |
|---|---|---|
| EP | 1034746 B1 | 3/2006 |
| EP | 1632191 A2 | 3/2006 |
| EP | 1065981 B1 | 5/2006 |
| EP | 1082944 B1 | 5/2006 |
| EP | 1652481 A2 | 5/2006 |
| EP | 1382303 B1 | 6/2006 |
| EP | 1253866 B1 | 7/2006 |
| EP | 1032318 B1 | 8/2006 |
| EP | 1045672 B1 | 8/2006 |
| EP | 1617768 B1 | 8/2006 |
| EP | 1693015 A2 | 8/2006 |
| EP | 1400214 B1 | 9/2006 |
| EP | 1702567 A2 | 9/2006 |
| EP | 1129665 B1 | 11/2006 |
| EP | 1400206 B1 | 11/2006 |
| EP | 1721568 A1 | 11/2006 |
| EP | 1256317 B1 | 12/2006 |
| EP | 1285633 B1 | 12/2006 |
| EP | 1728473 A1 | 12/2006 |
| EP | 1728475 A2 | 12/2006 |
| EP | 1479346 B1 | 1/2007 |
| EP | 1484024 B1 | 1/2007 |
| EP | 1754445 A2 | 2/2007 |
| EP | 1759812 A1 | 3/2007 |
| EP | 1767163 A1 | 3/2007 |
| EP | 1769756 A1 | 4/2007 |
| EP | 1769758 A1 | 4/2007 |
| EP | 1581128 B1 | 5/2007 |
| EP | 1780825 A1 | 5/2007 |
| EP | 1785097 A2 | 5/2007 |
| EP | 1790293 A2 | 5/2007 |
| EP | 1800610 A1 | 6/2007 |
| EP | 1300117 B1 | 8/2007 |
| EP | 1813199 A1 | 8/2007 |
| EP | 1813201 A1 | 8/2007 |
| EP | 1813202 A1 | 8/2007 |
| EP | 1813203 A2 | 8/2007 |
| EP | 1813207 A1 | 8/2007 |
| EP | 1813209 A1 | 8/2007 |
| EP | 1487359 B1 | 10/2007 |
| EP | 1599146 B1 | 10/2007 |
| EP | 1839596 A1 | 10/2007 |
| EP | 2110083 A2 | 10/2007 |
| EP | 1857057 A2 | 11/2007 |
| EP | 1402821 B1 | 12/2007 |
| EP | 1872727 A1 | 1/2008 |
| EP | 1897502 A1 | 3/2008 |
| EP | 1908417 A2 | 4/2008 |
| EP | 1330201 B1 | 6/2008 |
| EP | 1702568 B1 | 7/2008 |
| EP | 1943955 A2 | 7/2008 |
| EP | 1943957 A2 | 7/2008 |
| EP | 1943964 A1 | 7/2008 |
| EP | 1943976 A2 | 7/2008 |
| EP | 1593337 B1 | 8/2008 |
| EP | 1970014 A1 | 9/2008 |
| EP | 1980213 A2 | 10/2008 |
| EP | 1759645 B1 | 11/2008 |
| EP | 1990014 A2 | 11/2008 |
| EP | 1693008 B1 | 12/2008 |
| EP | 1759640 B1 | 12/2008 |
| EP | 2000102 A2 | 12/2008 |
| EP | 2005894 A2 | 12/2008 |
| EP | 2008595 A2 | 12/2008 |
| EP | 1736104 B1 | 3/2009 |
| EP | 1749486 B1 | 3/2009 |
| EP | 2039316 A2 | 3/2009 |
| EP | 1721576 B1 | 4/2009 |
| EP | 1733686 B1 | 4/2009 |
| EP | 2044890 A1 | 4/2009 |
| EP | 1550409 A1 | 6/2009 |
| EP | 1550413 B1 | 6/2009 |
| EP | 1745748 B1 | 8/2009 |
| EP | 2090237 A1 | 8/2009 |
| EP | 2090241 A1 | 8/2009 |
| EP | 2090244 A2 | 8/2009 |
| EP | 2090245 A1 | 8/2009 |
| EP | 2090256 A2 | 8/2009 |
| EP | 2095777 A2 | 9/2009 |
| EP | 2098170 A2 | 9/2009 |
| EP | 2110082 A1 | 10/2009 |
| EP | 2111803 A2 | 10/2009 |
| EP | 1813208 B1 | 11/2009 |
| EP | 1908426 B1 | 11/2009 |
| EP | 2116195 A1 | 11/2009 |
| EP | 1607050 B1 | 12/2009 |
| EP | 1815804 B1 | 12/2009 |
| EP | 1566150 B1 | 4/2010 |
| EP | 1813206 B1 | 4/2010 |
| EP | 1769754 B1 | 6/2010 |
| EP | 1535565 B1 | 10/2010 |
| EP | 1702570 B1 | 10/2010 |
| EP | 1785098 B1 | 10/2010 |
| EP | 2005896 B1 | 10/2010 |
| EP | 2030578 B1 | 11/2010 |
| EP | 1627605 B1 | 12/2010 |
| EP | 2286738 A2 | 2/2011 |
| EP | 1690502 B1 | 3/2011 |
| EP | 1769755 B1 | 4/2011 |
| EP | 1813205 B1 | 6/2011 |
| EP | 2090243 B1 | 6/2011 |
| EP | 2329773 A1 | 6/2011 |
| EP | 1908414 B1 | 11/2011 |
| EP | 2153781 B1 | 11/2011 |
| EP | 1785102 B1 | 1/2012 |
| EP | 2090253 B1 | 3/2012 |
| EP | 2005895 B1 | 8/2012 |
| EP | 2090248 B1 | 8/2012 |
| FR | 999646 A | 2/1952 |
| FR | 1112936 A | 3/1956 |
| FR | 2598905 A1 | 11/1987 |
| FR | 2765794 A | 1/1999 |
| GB | 939929 A | 10/1963 |
| GB | 1210522 A | 10/1970 |
| GB | 1217159 A | 12/1970 |
| GB | 1339394 A | 12/1973 |
| GB | 2109241 A | 6/1983 |
| GB | 2272159 A | 5/1994 |
| GB | 2284242 A | 5/1995 |
| GB | 2336214 A | 10/1999 |
| GB | 2425903 A | 11/2006 |
| JP | 50-33988 U | 4/1975 |
| JP | S 58500053 A | 1/1983 |
| JP | 61-98249 A | 5/1986 |
| JP | S 61502036 A | 9/1986 |
| JP | 63-203149 | 8/1988 |
| JP | 3-12126 A | 1/1991 |
| JP | 5-212039 A | 8/1993 |
| JP | 6007357 A | 1/1994 |
| JP | H 6-30945 A | 2/1994 |
| JP | H 6-121798 A | 5/1994 |
| JP | 7051273 A | 2/1995 |
| JP | 7-124166 A | 5/1995 |
| JP | 7-255735 A | 10/1995 |
| JP | 8-33642 A | 2/1996 |
| JP | 8033641 A | 2/1996 |
| JP | 8-164141 A | 6/1996 |
| JP | 8229050 A | 9/1996 |
| JP | 2000-14632 | 1/2000 |
| JP | 2000033071 A | 2/2000 |
| JP | 2000171730 A | 6/2000 |
| JP | 2000287987 A | 10/2000 |
| JP | 2000325303 A | 11/2000 |
| JP | 2001-514541 A | 9/2001 |
| JP | 2001286477 A | 10/2001 |
| JP | 2002143078 A | 5/2002 |
| JP | 2002369820 A | 12/2002 |
| JP | 2003-500153 A | 1/2003 |
| JP | 2003-521301 A | 7/2003 |
| JP | 2004-329624 A | 11/2004 |
| JP | 2004-344663 | 12/2004 |
| JP | 2005-028147 A | 2/2005 |
| JP | 2005-028149 A | 2/2005 |
| JP | 2005-505309 A | 2/2005 |

(56) References Cited

FOREIGN PATENT DOCUMENTS

| | | |
|---|---|---|
| JP | 2005505322 T | 2/2005 |
| JP | 2005103293 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005152416 A | 6/2005 |
| JP | 2005-523105 A | 8/2005 |
| JP | 2005524474 A | 8/2005 |
| JP | 2006-034975 A | 2/2006 |
| JP | 2006-218297 A | 8/2006 |
| JP | 2006-281405 A | 10/2006 |
| JP | 2007-117725 A | 5/2007 |
| JP | 2008-283459 A | 11/2008 |
| RU | 2008830 C1 | 3/1994 |
| RU | 2141279 C1 | 11/1999 |
| RU | 2187249 C2 | 8/2002 |
| RU | 2225170 C2 | 3/2004 |
| SU | 189517 A | 1/1967 |
| SU | 328636 A | 9/1972 |
| SU | 886900 A1 | 12/1981 |
| SU | 1009439 A | 4/1983 |
| SU | 1333319 A2 | 8/1987 |
| SU | 1377053 A1 | 2/1988 |
| SU | 1561964 A1 | 5/1990 |
| SU | 1708312 A1 | 1/1992 |
| SU | 1722476 A1 | 3/1992 |
| SU | 1752361 A1 | 8/1992 |
| WO | WO 82/02824 A1 | 9/1982 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15648 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/18893 A1 | 9/1994 |
| WO | WO 94/22378 A1 | 10/1994 |
| WO | WO 94/23659 A1 | 10/1994 |
| WO | WO 95/02369 A1 | 1/1995 |
| WO | WO 95/03743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/18344 A2 | 6/1996 |
| WO | WO 96/19151 A1 | 6/1996 |
| WO | WO 96/19152 A1 | 6/1996 |
| WO | WO 96/20652 A1 | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/06582 A1 | 2/1997 |
| WO | WO 97/10763 A1 | 3/1997 |
| WO | WO 97/10764 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |
| WO | WO 97/34533 A1 | 9/1997 |
| WO | WO 97/37598 A1 | 10/1997 |
| WO | WO 97/39688 A2 | 10/1997 |
| WO | WO 98/17180 A1 | 4/1998 |
| WO | WO 98/27880 A1 | 7/1998 |
| WO | WO 98/30153 A1 | 7/1998 |
| WO | WO 98/47436 A1 | 10/1998 |
| WO | WO 99/03407 A1 | 1/1999 |
| WO | WO 99/03408 A1 | 1/1999 |
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/03587 A1 | 1/2001 |
| WO | WO 01/05702 A1 | 1/2001 |
| WO | WO 01/10482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/91646 A1 | 12/2001 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/015604 A2 | 2/2003 |
| WO | WO 03/020106 A2 | 3/2003 |

(56) References Cited

FOREIGN PATENT DOCUMENTS

| | | |
|---|---|---|
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/086206 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/011037 A2 | 2/2004 |
| WO | WO 2004/019769 A1 | 3/2004 |
| WO | WO 2004/021868 A2 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A1 | 9/2004 |
| WO | WO 2004/078051 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/023486 A1 | 3/2006 |
| WO | WO 2006/027014 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/131110 A1 | 11/2007 |
| WO | WO 2007/137304 A1 | 11/2007 |
| WO | WO 2007/139734 A2 | 12/2007 |
| WO | WO 2007/142625 A2 | 12/2007 |
| WO | WO 2007/147439 A1 | 12/2007 |
| WO | WO 2008/021969 A2 | 2/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/070763 A1 | 6/2008 |
| WO | WO 2008/089404 A2 | 7/2008 |
| WO | WO 2008/101080 A1 | 8/2008 |
| WO | WO 2008/109125 A1 | 9/2008 |
| WO | WO 2008/124748 A1 | 10/2008 |
| WO | WO 2009/023851 A1 | 2/2009 |
| WO | WO 2009/0137761 A2 | 11/2009 |
| WO | WO 2010/030434 A1 | 3/2010 |
| WO | WO 2010/054404 A1 | 5/2010 |
| WO | WO 2010/063795 A1 | 6/2010 |
| WO | WO 2010/098871 A2 | 9/2010 |
| WO | WO 2012/021671 A1 | 2/2012 |
| WO | WO 2012/044844 A2 | 4/2012 |

OTHER PUBLICATIONS

Disclosed Anonymously, "Motor-Driven Surgical Stapler Improvements," Research Disclosure Database No. 526041, Published: Feb. 2008.

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, (2000), 3 pages.

"Biomedical Coatings," Fort Wayne Metals, Research Products Corporation, obtained online at www.fwmetals.com on Jun. 21, 2010 (1 page).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 a Polarized Relay, Copyright Matsushita Electric Works, Ltd. (Known of at least as early as Aug. 17, 2010), 5 pages.

ASTM procedure D2240-00, "Standard Test Method for Rubber Property-Durometer Hardness," (Published Aug. 2000).

ASTM procedure D2240-05, "Standard Test Method for Rubber Property-Durometer Hardness," (Published Apr. 2010).

International Search Report for PCT/US2012/028886, dated Nov. 23, 2012 (6 pages).

Covidien Brochure, "Endo GIA™ Reloads with Tri-Staple™ Technology," (2010), 1 page.

(56) References Cited

OTHER PUBLICATIONS

Covidien Brochure, "Endo GIA™ Reloads with Tri-Staple™ Technology and Endo GIA™ Ultra Universal Staplers," (2010), 2 pages.
Covidien Brochure, "Endo GIA™ Black Reload with Tri-Staple™ Technology," (2012), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Covidien Brochure, "Endo GIA™ Ultra Universal Stapler," (2010), 2 pages.

* cited by examiner

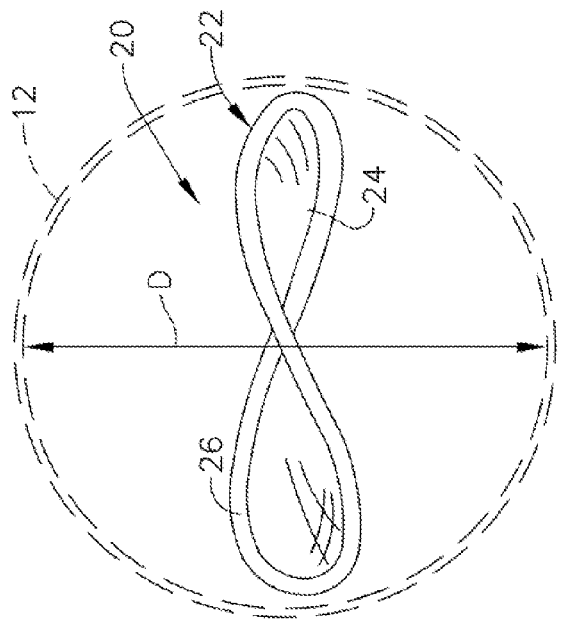
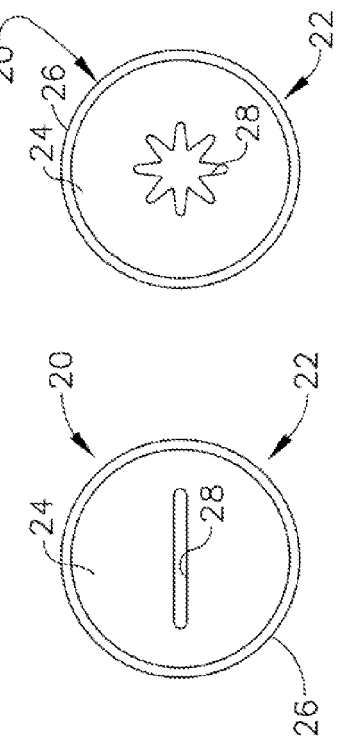
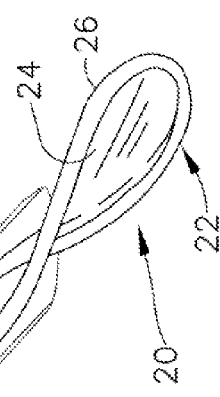
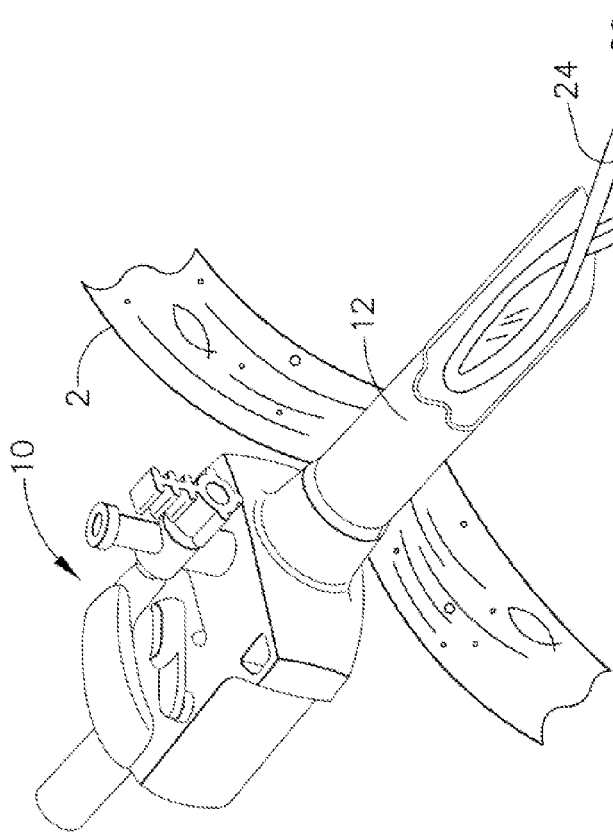
FIG. 2
FIG. 3
FIG. 4
FIG. 5

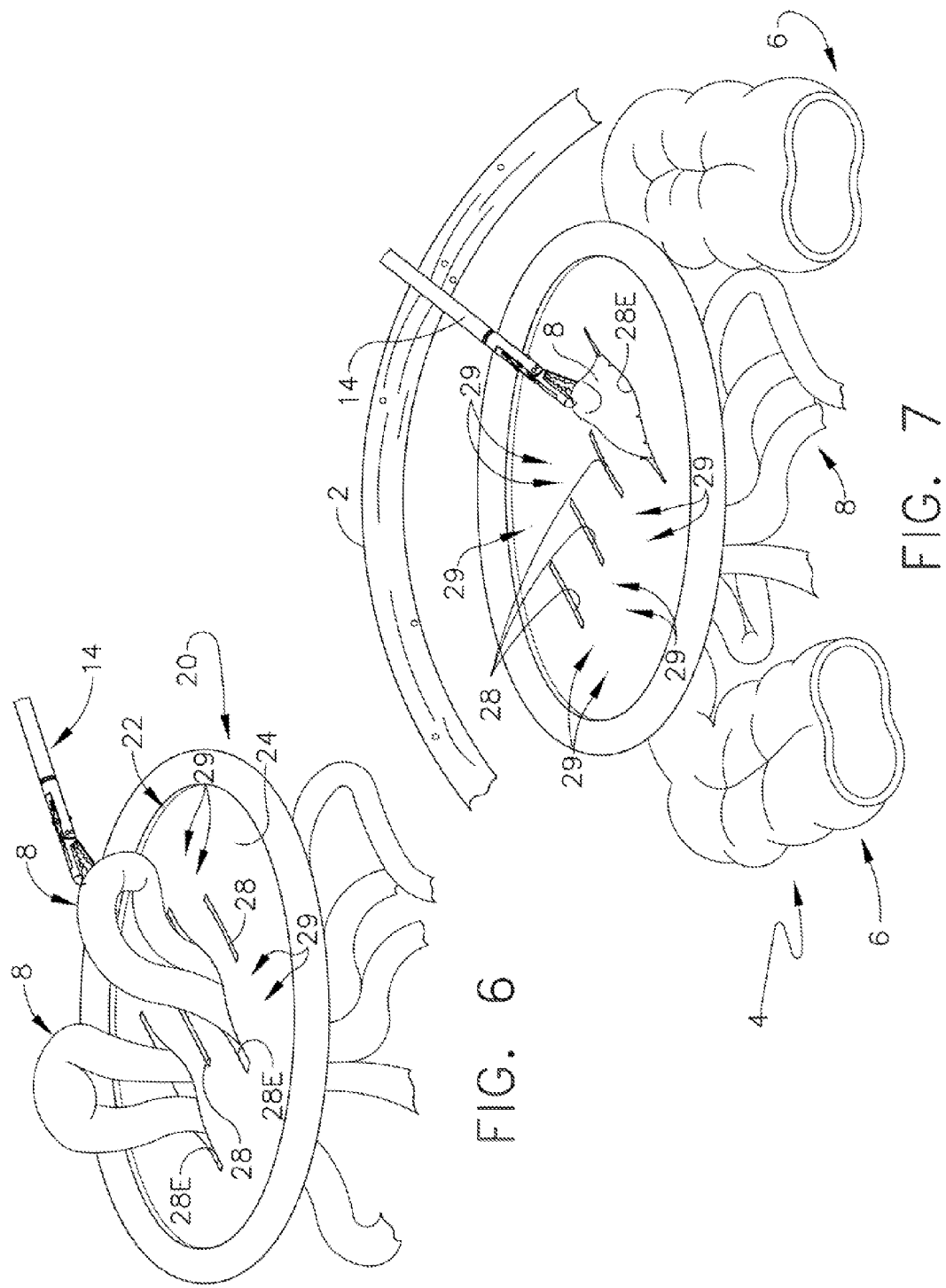

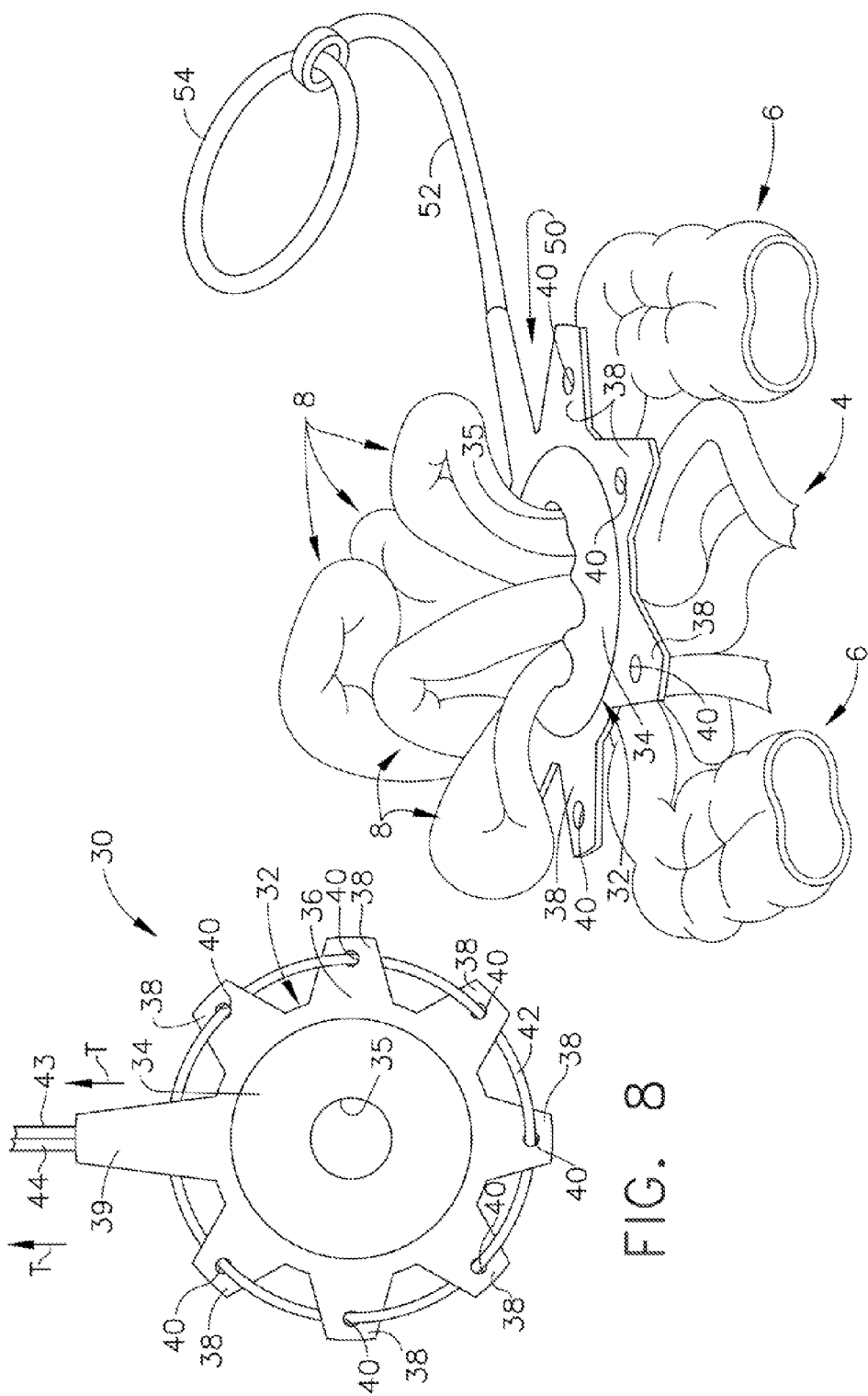

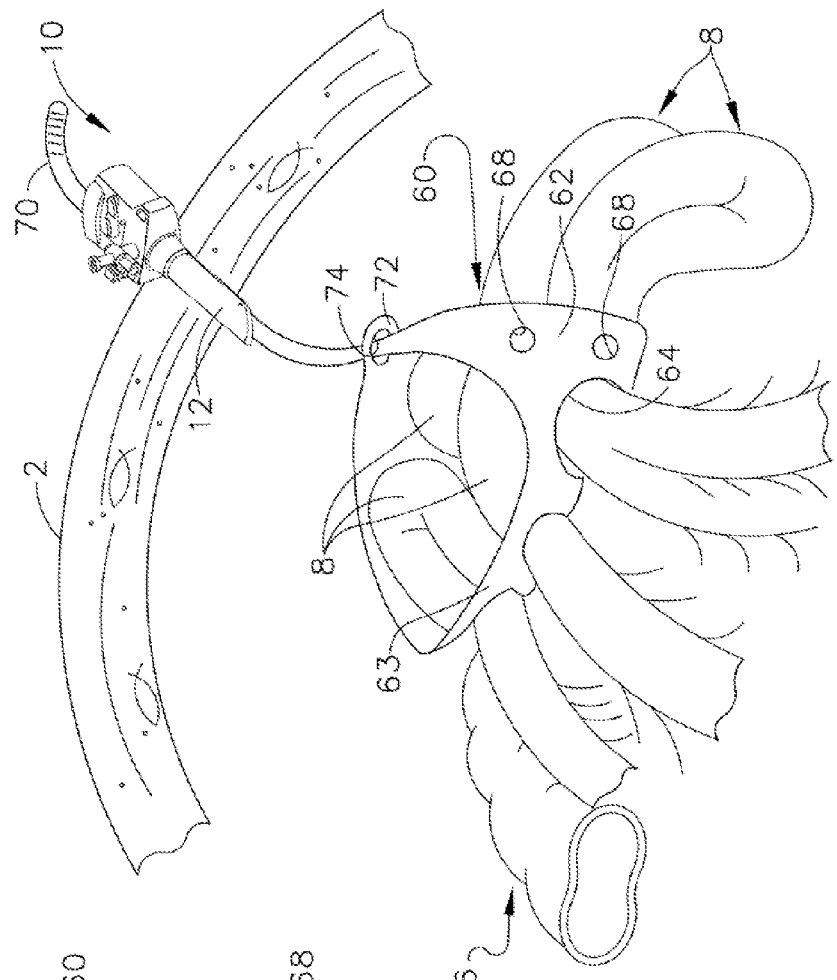
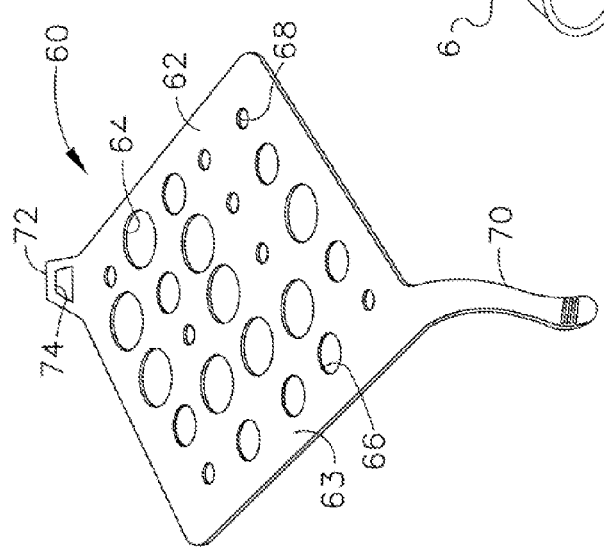
FIG. 10
FIG. 11

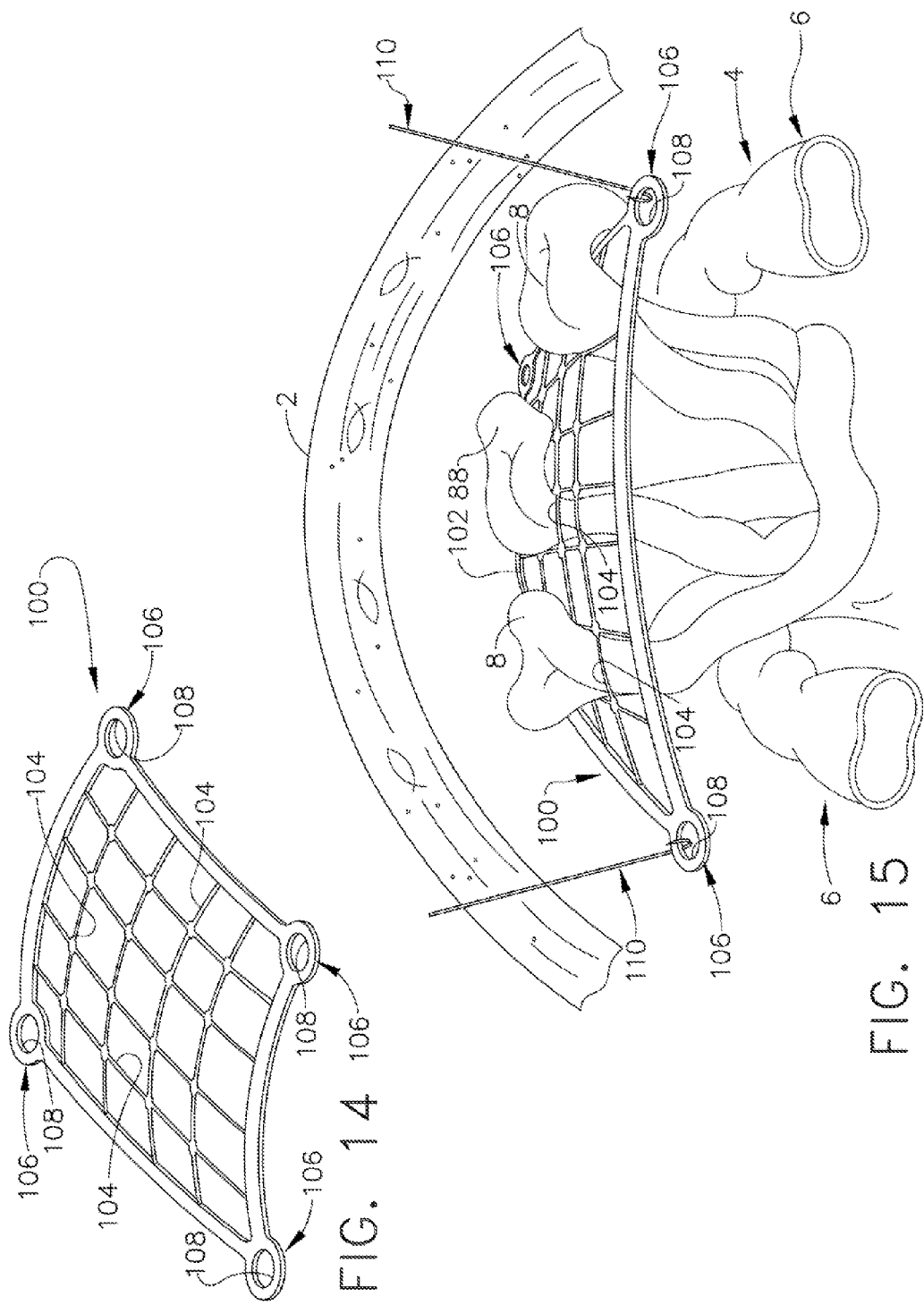

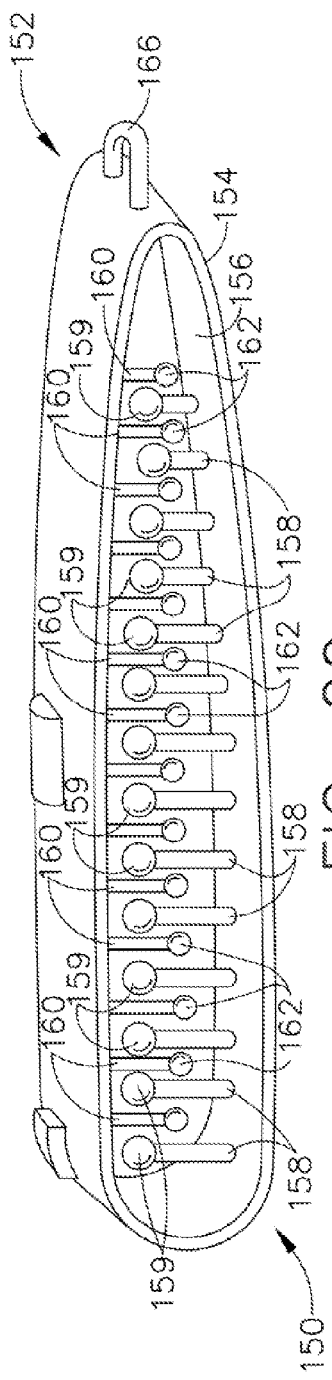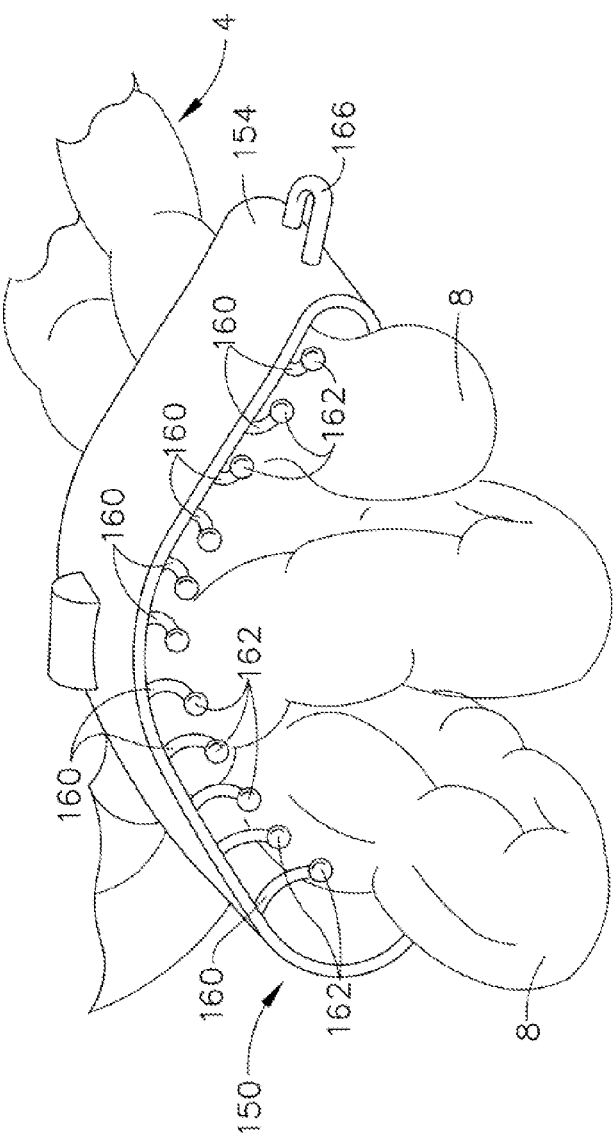

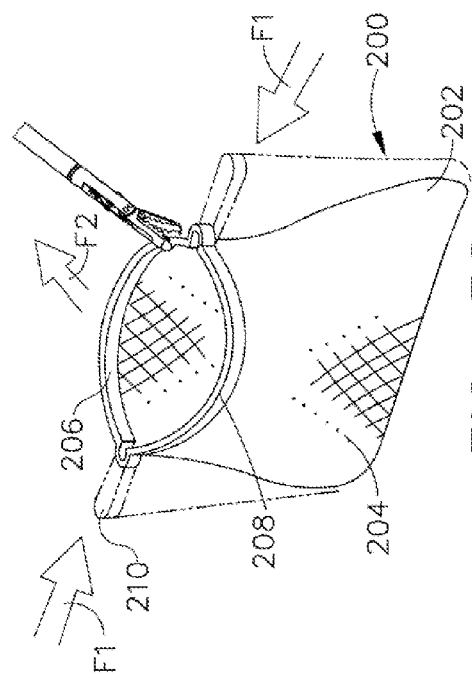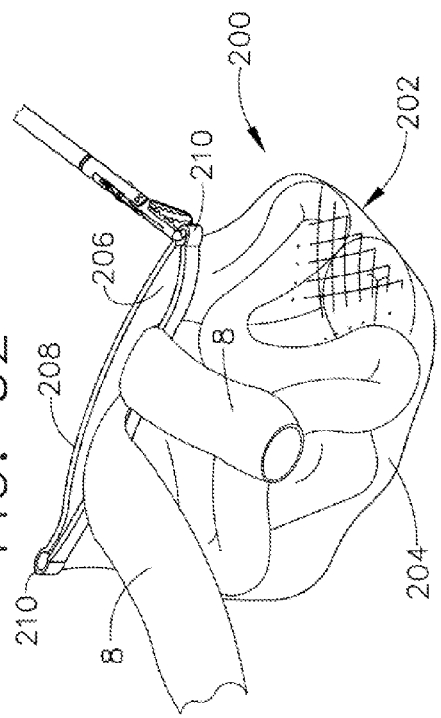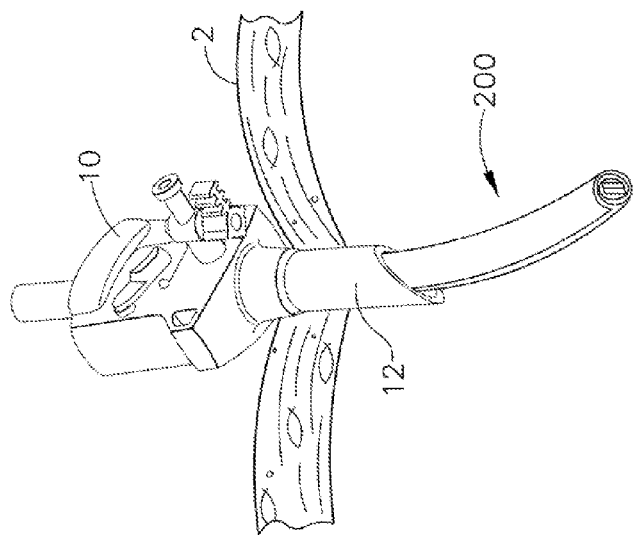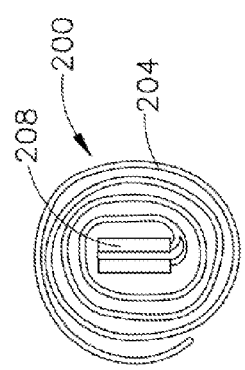

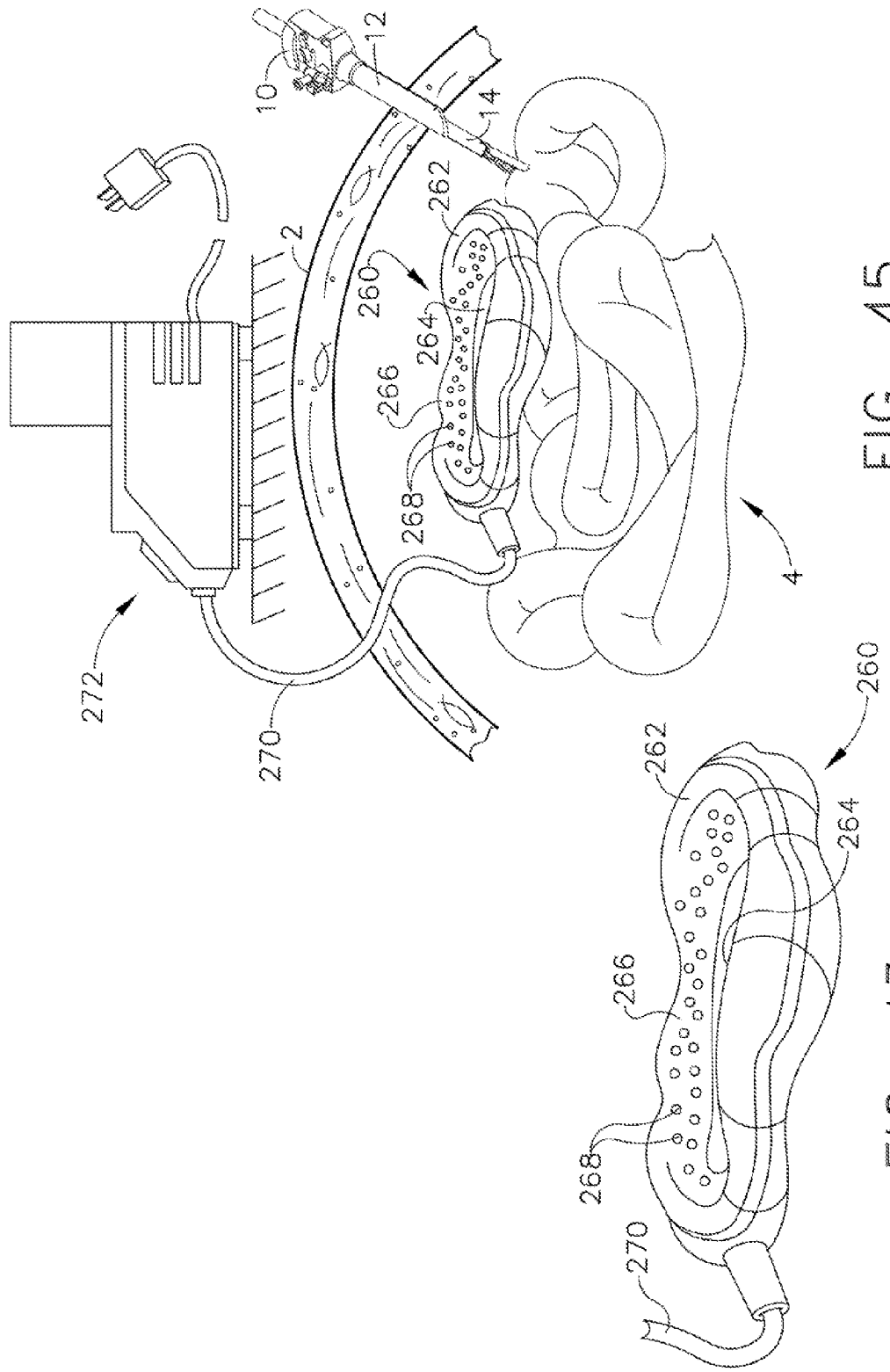

SURGICAL BOWEL RETRACTOR DEVICES

CROSS-REFERENCE TO RELATED APPLICATIONS

This non-provisional patent application claims the benefit of and priority from U.S. Provisional Patent Application Ser. No. 61/452,432, filed Mar. 14, 2011, entitled "Surgical Stapling Instruments", the entire disclosure of which is hereby incorporated by reference.

FIELD OF THE INVENTION

The present invention generally relates to surgical devices for temporarily retaining and supporting tissues and organs in a desired orientation during surgery, and more particularly, to devices for retracting portions of the bowel during surgery.

BACKGROUND

One major challenge to employing laparoscopic colorectal techniques is the ability to move all of the unrelated or non-involved tissue out of the surgical site to permit better physical and visual access to the target tissue or organ. In an open procedure, large metal retractors would be used to pull the masses of small intestines away and then pack them off with surgical sponges. When performing various colorectal surgical procedures, the surgeon often must manipulate the surgical instruments through a pile or collection of bowel to open up a window to operate in.

Thus, the need exists for devices that can be used to support portions of the bowel during laparoscopic colorectal operations in unobtrusive orientations to provide better physical and visual access to the portion of the bowel to be operated on.

The foregoing discussion is intended only to illustrate some of the shortcomings present in the field of the invention at the time, and should not be taken as a disavowal of claim scope.

BRIEF SUMMARY

In connection with general aspects of various embodiments of the present invention, there is provided a bowel retractor device that, in various forms, comprises an elastic body that is configurable from a first collapsed position wherein the elastic body is insertable through an opening in a patient's body to a second expanded position wherein a portion of the patient's bowel may be supported by a central portion of the elastic body in a desired orientation.

In connection with yet another general aspect of one form of the present invention, there is provided a bowel retractor device that includes a central portion that has a first plurality of flexible first arms protruding therefrom in a first direction. The plurality of first flexible arms defines a first opening between each adjacent flexible arm. A second plurality of flexible second arms protrude from the central portion in a second direction wherein each flexible second arm protrudes from the central portion at positions opposite from the first openings and wherein the flexible second arms are spaced from each other to form a second opening therebetween.

In accordance with still another general aspect of one form of the present invention, there is provided a bowel retractor device that includes a selectively inflatable ring that has a textured annular surface that defines an interior area. A supply conduit is coupled to the selectively inflatable ring and a source of pressurized medium.

In accordance with other general aspects of various forms of the present invention, there is provided a method for performing laparoscopic bowel surgery on a target portion of a patient's bowel. In one form of the present invention, the method includes inserting at least one bowel retractor device through an opening in the patient. Each of the bowel retractor devices comprises a body that is configurable from a first collapsed position wherein the body is insertable through the opening to a second expanded position. The method further includes engaging a corresponding non-target portion of the bowel with a central portion of each of the at least one bowel retractor devices when in the second expanded position and positioning the at least one bowel retractor device to locate the corresponding non-target bowel portion engaged thereby in non-obtrusive positions to thereby provide physical and visual access to the target portion of the bowel.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 2 is a perspective view showing a conventional trocar installed through the abdominal wall of a patient and being used to pass a bowel retractor embodiment of the present invention into a surgical area within the abdomen;

FIG. 3 is a view of a bowel retractor embodiment of the present invention inserted in a twisted orientation into a cannula of a trocar;

FIG. 4 is a top view of a bowel retractor device embodiment of the present invention;

FIG. 5 is a top view of another bowel retractor device embodiment of one form of the present invention;

FIG. 6 is a perspective view of another bowel retractor device embodiment with non-target portions of a patient's bowel supported therein;

FIG. 7 is another perspective view of a bowel retractor device located inside a patient's abdomen and wherein the surgeon is using a grasping device to pull non-target portions of the patient's bowel through an opening in the bowel retractor device;

FIG. 8 is a top view of another bowel retractor device embodiment of the present invention;

FIG. 9 is a perspective view of the bowel retractor device of FIG. 8 supporting non-target portions of a patient's bowel therein;

FIG. 10 is a front perspective view of another bowel retractor device embodiment of the present invention;

FIG. 11 is a perspective view of the bowel retractor device of FIG. 10 supporting non-target portions of a patient's bowel therein and wherein the tether portion thereof has be inserted through the cannula of a trocar;

FIG. 14 is a perspective view of another bowel retractor device embodiment of the present invention;

FIG. 15 is a perspective view of the bowel retractor device of FIG. 14 supporting non-target portions of a patient's bowel therein and wherein retractor manipulation needles have been inserted through the abdominal wall to engage portions of the bowel retractor device;

FIG. 20 is a side view of another bowel retractor device embodiment of the present invention;

FIG. 21 is a perspective view of the bowel retractor device embodiment of FIG. 20 with portions of a patient's bowel supported therein;

FIG. 32 is a perspective view of another bowel retractor device embodiment of the present invention in an open position and supported by a grasping instrument;

FIG. 33 is another perspective view of the bowel retractor device embodiment of FIG. 32 and supporting a bowel portion therein;

FIG. 34 is a partial perspective view of a trocar device inserted through a portion of a patient's abdominal wall with the bowel retractor device of FIGS. 32 and 33 being inserted through the trocar cannula;

FIG. 35 is a top view of the bowel retractor device embodiment of FIGS. 32-34 in a collapsed or rolled-up position wherein the retractor device may be inserted through a trocar cannula or other opening in a patient's body;

FIG. 43 is a perspective view of a portion of another bowel retractor device embodiment of the present invention in an uninflated state;

FIG. 45 is a partial perspective view of a portion of a patient's abdomen supporting the bowel retractor device embodiment of FIG. 43 therein in an uninflated state.

DETAILED DESCRIPTION

Figure 1:
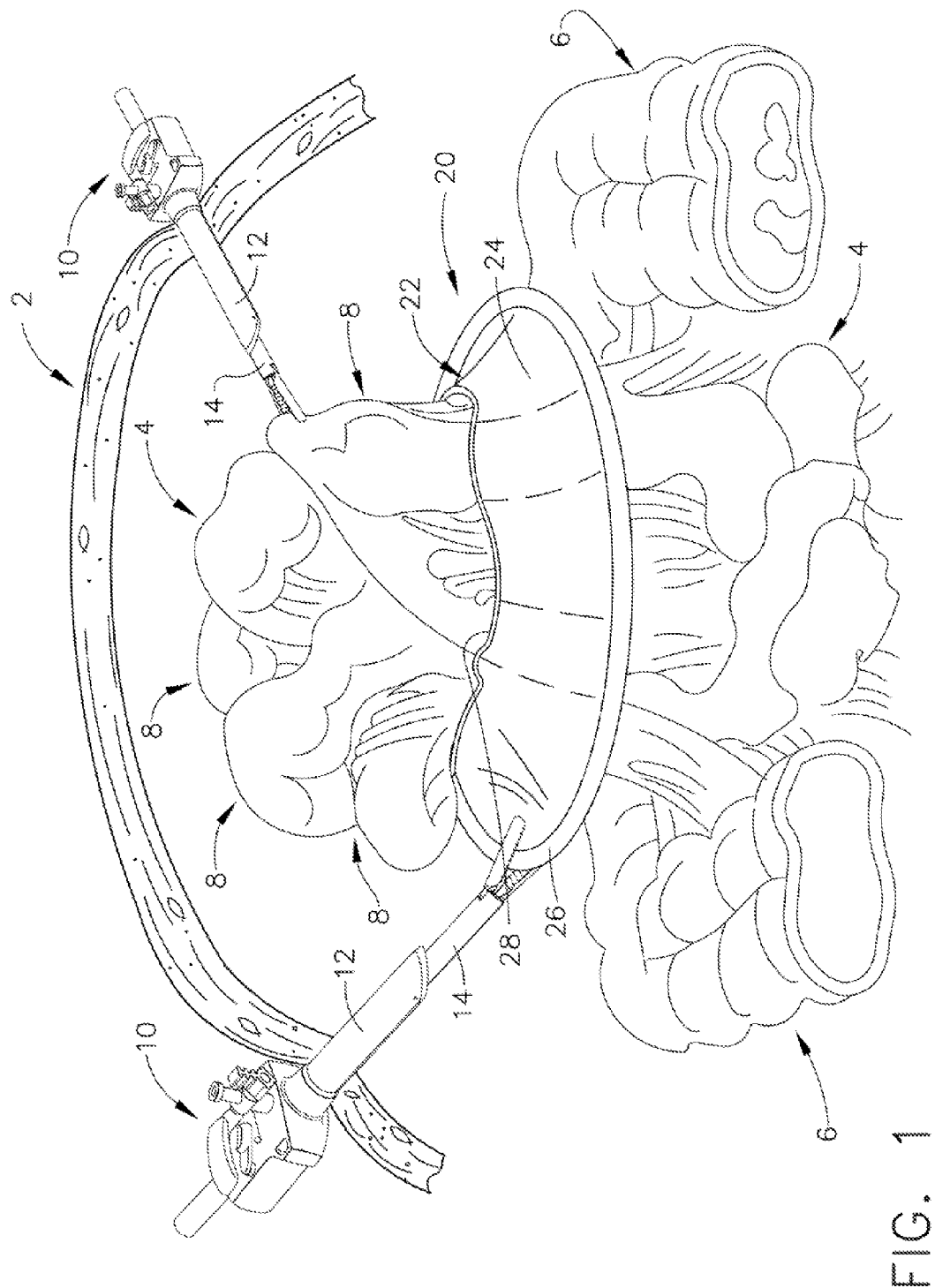
FIG. 1 is a view of a portion of a patient's abdomen and bowel segment with two trocars installed through the abdominal wall and one of the bowel retraction device embodiments of the present invention with non-target portions of the patient's bowel installed therein.

The assignee of the present application also owns the following applications which were contemporaneously filed herewith and which are each herein incorporated by reference in their respective entireties:

U.S. patent application Ser. No. 13/181,779, filed Jul. 13, 2011, now U.S. Patent Publication No. 2012/0234892, entitled "Multiple Part Anvil Assemblies For Circular Surgical Stapling Devices;

U.S. patent application Ser. No. 13/181,798, filed Jul. 13, 2011, now U.S. Patent Publication No. 2012/0239010, entitled "Modular Surgical Tool Systems;

U.S. patent application Ser. No. 13/181,801, filed Jul. 13, 2011, now U.S. Patent Publication No. 2012/0238826, entitled "Trans-Rectum Universal Ports";

U.S. patent application Ser. No. 13/181,807, filed Jul. 13, 2011, now U.S. Patent Publication No. 2012/0238829, entitled "Modular Tool Heads For Use With Circular Surgical Instruments";

U.S. patent application Ser. No. 13/181,831, filed Jul. 13, 2011, now U.S. Patent Publication No. 2012/0239082, entitled "Tissue Manipulation Devices";

U.S. patent application Ser. No. 13/181,768, filed Jul. 13, 2011, now U.S. Patent Publication No. 2012/0234890, entitled "Collapsible Anvil Plate Assemblies For Circular Surgical Stapling Devices";

U.S. patent application Ser. No. 13/181,786, filed Jul. 13, 2011, now U.S. Patent Publication No. 2012/0234898, entitled "Circular Stapling Devices With Tissue-Puncturing Anvil Features;

U.S. patent application Ser. No. 13/181,774, filed Jul. 13, 2011, now U.S. Patent Publication No. 2012/0234891, entitled "Anvil Assemblies With Collapsible Frames For Circular Staplers";

U.S. patent application Ser. No. 13/181,842, filed Jul. 13, 2011, now U.S. Patent Publication No. 2012/0239075, entitled "Rectal Manipulation Devices"; and U.S. patent application Ser. No. 13/181,836, filed Jul. 13, 2011, now U.S. Patent Publication No. 2012/0238823, entitled "Surgical Access Devices With Anvil Introduction and Specimen Retrieval Structures"

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included . in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

FIG. 1 illustrates a portion of a patient's abdominal wall 2 and portions of the patient's bowel or colon 4. More specifically, a bowel retractor device 20 embodiment of the present invention is employed to support/retract non-target bowel portions 8 from target bowel portions 6. As used herein, the term "target bowel portion(s)" refers to that portion or portions of the bowel on which the surgical procedure is to be performed. The term "non-target bowel portions" refers to those portions of the bowel that are not the subject of the surgical procedure and which often obscure physical and/or visual access to the target portions. In the depicted Figure, two conventional trocar devices 10 have been inserted through the abdominal wall 2. Such trocar devices 10 include a cannula 12 that is configured to form of a passage through the abdominal wall 2 through which surgical instruments 14 may be inserted. A variety of styles and sizes of trocars are known. In general, the trocars are sized based on the inner diameter of their respective cannula.

In various non-limiting embodiments, the bowel retractor device 20 comprises an elastic body portion 22 that is configurable from a first collapsed orientation that permits the elastic body portion 22 to be inserted through a trocar cannula 12 to a second expanded position wherein a non-target portion or portions 8 of a patient's bowel 4 are supported by a central portion 24 of the bowel retractor device 20. In various embodiments, the central portion 24 may comprise a substantially flexible film such as for example silicone or neoprene film having a thickness ranging from, for example, 0.020 inches to 0.120 inches that has a collar or flexible outer ring 26 formed therearound. The flexible outer ring 26 may comprise for example in at least one embodiment, an embedded stainless steel wire or titanium wire. In at least one embodiment, when the retractor device 20 is in the first or collapsed position, it is in a twisted configuration such as those shown in FIGS. 2 and 3. When the retractor device 20 is in the second or expanded position, the retractor device 20 may assume the positions shown in FIGS. 1, 4, and 5. The flexible central portion 24 has a first amount of elasticity and the flexible outer ring 26 has a second amount of elasticity. In some embodiments, the second amount of elasticity is less than the first amount of elasticity. That is the outer ring 26 may be more rigid that the flexible central portion 24.

As can be seen in FIGS. 4 and 5, the central portion 24 of the bowel retractor device 20 has at least one opening 28 therein. The size, shape, number, and orientation(s) of such opening(s) may vary. For example, in FIG. 4, the opening 28 comprises an elongated slot and the opening 28 in FIG. 5 has a multiple-pointed star shape.

The retractor devices 20 may be used as follows in connection with one exemplary method of the present invention. To commence the surgical process, at least two trocars 10 are installed through the patient's abdominal wall 2 in a known manner. One of the trocars 10 may be initially used to pass the retractor device or devices 20 therethrough. The other trocar 10 may be used to enable the surgeon to pass a conventional surgical instrument such as a grasper 14 to grab the retractor device 20 and position it over the non-target bowel portions 8. Once the retractor device 20 has exited the trocar cannula 12, the surgeon may also use that trocar 10 to pass a second grasper 14 therethrough to assist in drawing the non-target portions 8 of bowel through the opening(s) 28 in the retractor device 20. Such arrangement enables the non-target bowel portions 8 to be retained away from the target bowel portions 6. By introducing three or four of the retractor devices 20, for example, multiple quadrants of non-target bowel portions 8 could be tucked away and easily movable to clear the surgical site. The coupled group could be pulled en masse to one side or the other of the target bowel portion(s) 6 making it very easy to negotiate the multiple bowel quadrants to perform the surgical procedure on the target bowel portions 6. In various embodiments, the surgeon may pull one section 8 of bowel 4 multiple times through the opening 26 to bunch up and constrain that non-target portion 8 of the bowel 4.

In some embodiments, the outer ring or collar 26 may be bendable as opposed to being purely elastic. For example, in some embodiments, the collar 26 may comprise a bendable metal wire or cable that is encapsulated in a flexible material such as silicone, neoprene, etc. In such arrangement, the surgeon may bend or twist the collar or outer ring 26 into a desired configuration and the metal wire will retain it in that configuration. Once the retractor device 20 has been fully inserted into the patient, the surgeon may bend the retractor device 20 into whatever restraining form that would be most useful to keep the clump of non-target bowel 8 out of the working space. For example, the retractor device 20 may be folded or bent and then lodged up behind the trocar cannula 12 or held back with a grasping instrument 14, whichever is more convenient. The flexible fit holds the non-target bowel portion 8 together without strangulating it or interfering with the peristalsis which might cause swelling. The fit between the non-target portion(s) 8 pulled through the opening(s) is such that the non-target bowel portion(s) would not slip back out of the opening 28.

FIGS. 6 and 7 illustrate bowel retractor devices 20 with alternative opening arrangements. In particular, the openings 28 comprises a plurality of slots and perforations 29. The perforations 29 are aligned off of each end of the slots 28 as shown and enable the flexible center portion 24 to rupture to enable the slots 28 to enlarge or expand as needed as the bowel portions 8 are pulled therethrough. In FIGS. 7 and 8, those slots that have expanded are designated as slots "28E".

FIG. 8 illustrates another retractor device 30 embodiment of the present invention that includes a body portion 32 that is configurable from a first collapsed orientation that permits the body portion 32 to be inserted through a trocar cannula or other opening in a patient's body to a second expanded position wherein a non-target portion or portions 8 of a patient's bowel 4 are supported by a central portion 34 of the bowel retractor device 30. In various embodiments, the central portion 34 may comprise a substantially flexible film such as, for example, a silicone or neoprene film having a thickness ranging from, for example, 0.020 inches to 0.120 inches that has a collar or flexible outer ring 36 formed therearound. As can be seen in FIG. 8, the outer collar 36 is formed with a plurality of spaced radially outwardly extending tabs 38. Each tab 38 has a hole 40 therethrough that is configured to receive a cinchable member 42 such as, for example, a vectran, nylon, polyglycolic acid (PGA), catgut, or polypropylene cable to be woven therethrough as shown. The end portions 43, 44 of the cinchable member 42 pass through a grommet portion 39 of the collar 36. By applying tension "T" to the end portions 43, 44 will cause the bowel retractor 30 to be cinched around the non-target bowel portions 8 pulled through an opening 35 in the central portion 34. The cinchable member 42 may also be used to manipulate the retractor 30 and retrain it in a desired position.

In FIG. 9, the bowel retractor device 50 is substantially similar to the bowel retractor device 30, except that the bowel retractor device 50 lacks the cinchable member. Instead a flexible tether 52 extends from the device 50. The tether has a manipulation ring 54 attached thereto as shown. The outwardly extending tabs 38 form portions of the device 50 that may be easily grasped with a grasping instrument to facilitate the installation, manipulation and positioning of the bowel retractor device 50.

FIGS. 10 and 11 illustrate another bowel retractor device embodiment 60 of the present invention. The bowel retractor 60 includes an elastic body portion 62 that comprises a flexible plate member 63 that has a plurality of openings 64, 66, 68 therethrough. In various embodiments, the flexible plate member 63 may comprise, for example, a silicone or neoprene film having thicknesses that range from 0.020 inches to 0.150 inches. In the illustrated embodiment, three different sizes of openings are shown. In other embodiments, all of the openings may have the same size and/or have different shapes. The scope of this embodiment of the present invention is intended to cover embodiments with a variety of differently-shaped openings and different arrangements of openings—having the same size and having different sizes. As can be further seen in FIGS. 10 and 11, a tether 70 is attached to other otherwise formed with the body portion 62 such that it protrudes therefrom. In addition, a retention tab or portion 72 is also formed on or attached to the body portion 62. In the illustrated embodiment, the body portion 62 is substantially square-shaped and the tether 70 and retention tab 72 are formed on opposite corners of the plate member 63.

The bowel retractor device 60 may be used as follows. After the device 60 has been inserted through the trocar 10 or otherwise located at the surgical site, the surgeon may use graspers or other surgical instruments to draw the non-target portions 8 of the patient's bowel 4 through one or more of the openings 64, 66, 68 in the body portion 62 in the manner described above. Once the non-target bowel portion(s) 8 have been drawn through one or more of the openings 64, 66, 68 the surgeon may loop the tether 70 through an opening 74 in the retention tab 72 and extend the tether 70 back through the trocar cannula 12 to enable the surgeon to retain, manipulate and/or position the retractor device 60 and retained non-target bowel portion(s) 8 from outside of the patient.

Figure 13:
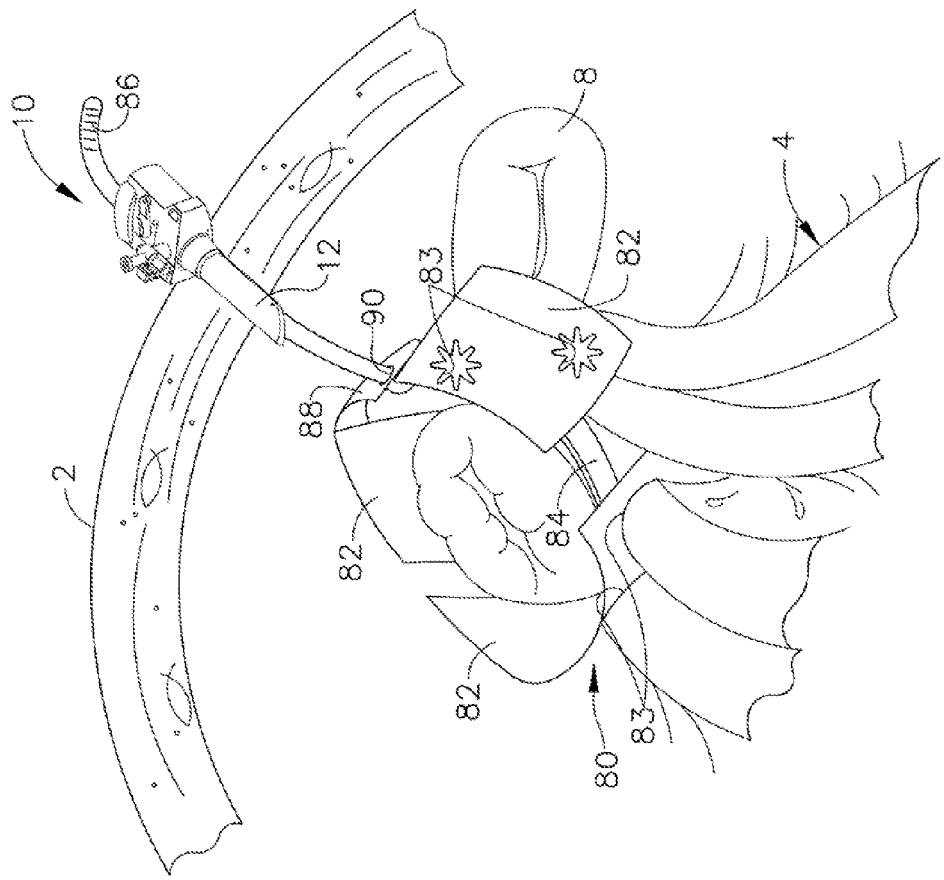
FIG. 13 is a perspective view of the bowel retractor device of FIG. 12 supporting non-target portions of a patient's bowel therein and wherein the tether portion thereof has be inserted through the cannula of a trocar.
Figure 12:
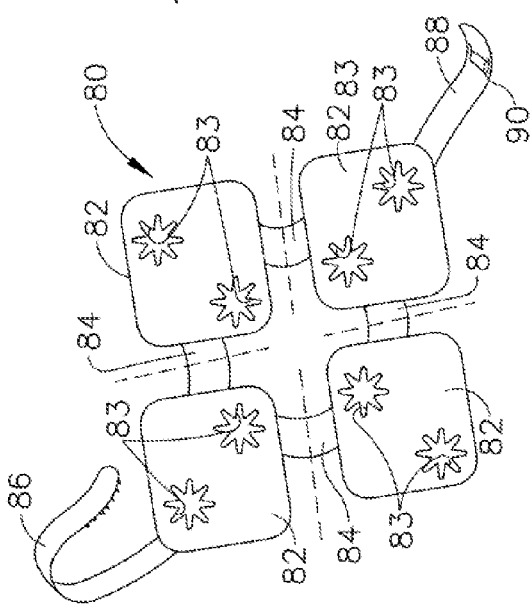
FIG. 12 is a top view of another bowel retractor device embodiment of the present invention.

FIGS. 12 and 13 illustrate another bowel retractor device embodiment 80 of the present invention. As can be seen in FIG. 12, in at least one embodiment, the device 80 comprises a plurality of (four are shown) of flexible plate members 82 that are interconnected by flexible straps 84. Each plate member 82 has at least one (two are shown) openings 83 therein. The openings 83 shown have a multiple pointed star shape. The number, shape and orientation of openings 83 may vary. One or more plate members 82 may have different numbers of differently shaped openings in arrangements that differ from the openings and arrangements in one or more other plate members 82. In still other embodiments, at least one plate member 82 has at least one opening 83 therethrough. As can also be seen in FIG. 12, a tether 86 is attached to, or is otherwise formed with, one of the plate members 82 such that it protrudes therefrom In addition, a retention strap 88 is attached to, or is otherwise formed with, another plate member 82. In the illustrated embodiment, the four plate members 82 are shown and the tether 86 and retention strap 72 are formed on the corners of opposite plate members 82.

The bowel retractor device 80 may be used as follows. After the device 80 has been inserted through the trocar 10 or otherwise located at the surgical site, the surgeon may use graspers or other surgical instruments to draw the non-target portions 8 of the patient's bowel 4 through one or more of the openings 83 in the plate members 82 in the manner described above. Once the non-target bowel portion(s) 8 have been drawn through one or more of the openings 83, the surgeon may loop the tether 86 through an opening 90 in the retention strap 88 and extend the tether 86 back through the trocar 10 to enable the surgeon to retain, manipulate and/or position the device and retained non-target bowel portion(s) 8 from outside of the patient.

FIGS. 14 and 15 illustrate another bowel retractor embodiment 100 of the present invention. The bowel retractor 100 includes a body portion 102 that comprises a flexible mesh portion that has a plurality of openings 104 therethrough. In various embodiments, the body portion may be fabricated from, for example, silicone, neoprene, etc. In the illustrated embodiment, openings 104 may be are arranged in a grid-like fashion. In other embodiments, the openings may have different sizes. The scope of this embodiment of the present invention is intended to cover embodiments with a variety of differently-shaped openings and different arrangements of openings—having the same size and having different sizes. As can be further seen in FIGS. 14 and 15, at least one manipulation formation 106 is formed on the body portion 102. In the illustrated embodiment, the device 100 is substantially square-shaped and a manipulation formation 106 is formed on each corner thereof. Each manipulation formation 106 has a hole 108 therethrough to enable a manipulation tool to engage and manipulate the device 100. The manipulation tool may comprise a grasper or other surgical instrument. In the illustrated embodiment, two needle-like hook members 110 are inserted through the patient's abdominal wall and serve to hook the openings 108 in the manipulation formations 106.

The bowel retractor device 100 may be used as follows. After the device 100 has been inserted through the trocar 10 or otherwise located at the surgical site, the surgeon may use graspers or other surgical instruments to draw the non-target portions 8 of the patient's bowel 4 through one or more of the openings 104 in the body portion 102 in the manner described above. Once the bowel portions 8 have been drawn through one or more of the openings 104, the surgeon may insert one or more of the needle-like hook members 110 through the abdominal wall 2 to hookingly engage one or more of the manipulation formations 106 to position and or retain the device 100 in a desired orientation.

Figure 16:
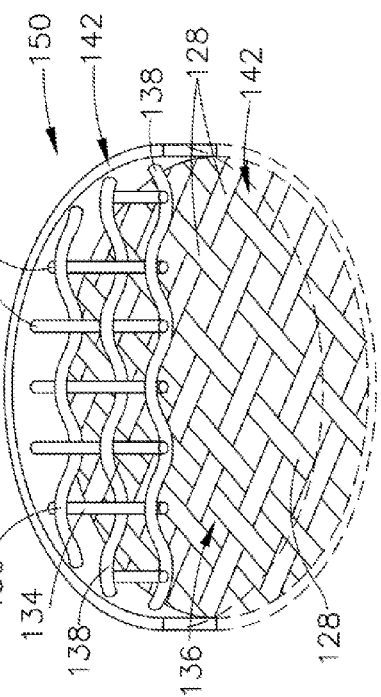
FIG. 16 is a perspective view of another bowel retractor device embodiment of the present invention.

FIG. 16 illustrates another bowel retractor device embodiment 120 of the present invention. The bowel retractor device 120 includes a body portion 122 that comprises a flexible annular ring 124 that has a flexible central portion 126 attached thereto. In at least one embodiment, the flexible central portion 126 comprises a plurality of interwoven flexible ribbon-like members 128. In various embodiments, the flexible annular ring may be fabricated from, for example, Polypropylene, Santoprene, etc. The interwoven ribbon members 128 will have weave tightness that permits non-target portion(s) 8 of the patient's bowel to be pulled therethrough without damaging the bowel, yet retain the non-target bowel portion(s) in position. To assist the surgeon with the manipulation and support of the device 120, a manipulation formation 129 may be formed on the annular ring 124 as shown.

The bowel retractor device 120 may be used as follows. After the device 120 has been inserted through the trocar 10 or otherwise located at the surgical site, the surgeon may use graspers or other surgical instruments to draw the non-target portions 8 of the patient's bowel 4 between the ribbons 128 in the manner described above. Once the bowel portions 8 have been drawn between the ribbons 128, the surgeon may use a grasper or other surgical instrument to engage the manipulation formation 129 to position and or retain the device 120 in a desired orientation.

Figure 17:
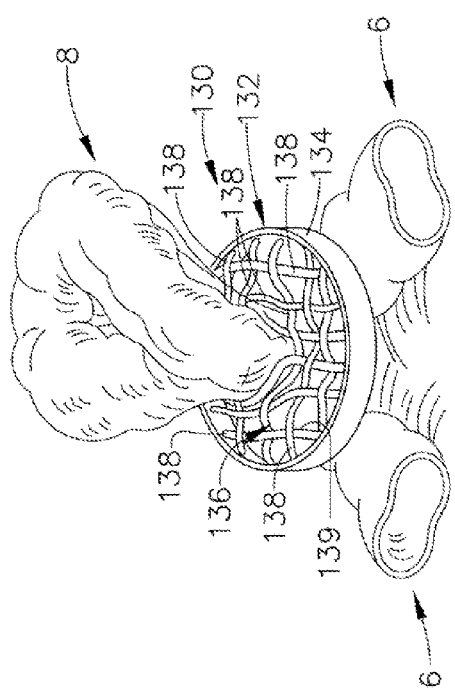
FIG. 17 is another perspective view of the bowel retractor device embodiment of FIG. 16 with a non-target portion of a patient's bowel being supported thereby.

FIG. 17 illustrates another bowel retractor device embodiment 130 of the present invention. The bowel retractor device 130 includes a body portion 132 that comprises a flexible annular ring 134 that has a flexible central portion 136 attached thereto. In at least one embodiment, the flexible central portion 136 comprises a plurality of interwoven flexible strips 138. In various embodiments, the flexible annular ring 134 may be fabricated from, for example, Santoprene, polypropylene, etc. In at least one embodiment, the interwoven flexible strips 138 have a substantially circular cross-sectional shape. The interwoven strips 138 define a plurality of openings 139 and will have weave tightness that permits non-target portion(s) 8 of the patient's bowel 4 to be pulled through one or more of the openings 139 without damaging the bowel, yet retain the bowel in position. To assist the surgeon with the manipulation and support of the device 120, a manipulation formation (not shown) may be formed on the annular ring 134 as shown.

The bowel retractor device 130 may be used as follows. After the device 130 has been inserted through the trocar 10 or otherwise located at the surgical site, the surgeon may use graspers or other surgical instruments to draw the non-target portions 8 of the patient's bowel 4 through one or more of the openings 139 in the manner described above. Once the non-target bowel portion(s) 8 have been drawn between the flexible strips 138, the surgeon may use a grasper or other surgical instrument to engage the manipulation formation to position and or retain the device 130 in a desired orientation.

Figure 18:
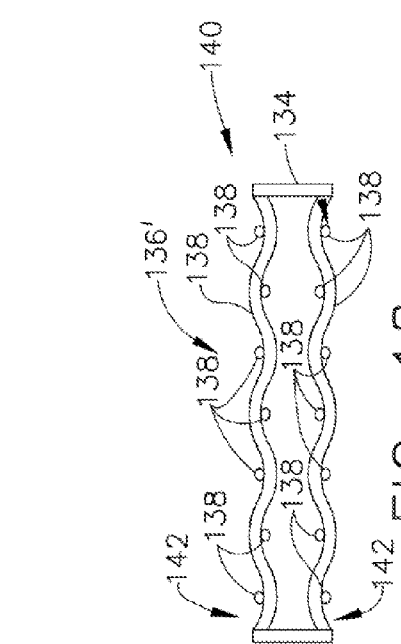
FIG. 18 is a cross-sectional view of the bowel retractor device embodiment of FIG. 16.
Figure 19:
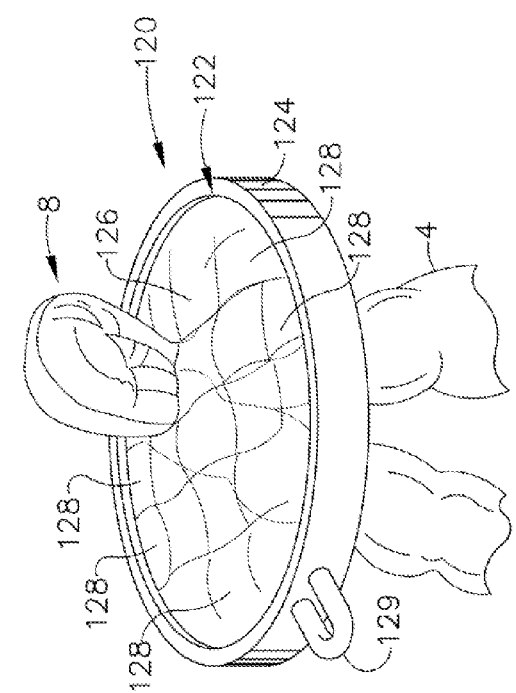
FIG. 19 is a partial perspective view of another bowel retractor device embodiment of the present invention.

FIG. 18 illustrates another bowel retractor device embodiment 140 of the present invention which is substantially similar to the bowel retractor device 130 described above except that the central portion 136' comprises a plurality of layers 142 of interwoven flexible strips 138. The bowel portions 8 may be drawn through the openings 139 in one or more of the layers 142. FIG. 19 illustrates another bowel retractor device embodiment 150 of the present invention which is substantially similar to the bowel retractor device 140 described above, except that one of the layers 142 comprises a plurality of interwoven ribbons 128 and another layer 142 comprises a plurality of interwoven flexible strips 138.

FIG. 20 illustrates another bowel retractor device embodiment 150 of the present invention. The bowel retractor device 150 includes a body portion 152 that comprises a flexible endless collar member 154 that defines an inner area 156. In various embodiments, the flexible endless collar member 154 is elongated and is sized to be passed down through a trocar cannula 12 or other opening through the abdominal wall 2. The flexible endless collar member 154 may be fabricated from, for example, Santoprene, polypropylene, etc. The device 150 further includes a plurality of flexible fingers 156, 160 that protrude inwardly from the endless collar member 154. In at least one embodiment, the flexible fingers 158 extend between fingers 160 and have a cross-sectional size that differs from a cross-sectional size of fingers 160. Also in various embodiments, each of the fingers 158 have a ball-shaped member 159 formed on the end thereof and each of the fingers 160 have a ball-shaped member 162 formed on the end thereof. In at least one embodiment, each of the ball-shaped members 159 have a diameter that differs from the diameter of the ball-shaped members 162.

The bowel retractor device 150 may be used as follows. After the device 150 has been inserted through the trocar 10 or otherwise located at the surgical site, the surgeon may use graspers or other surgical instruments to draw the non-target portions 8 of the patient's bowel 4 through the central area 156. Once the non-target bowel portions 8 have been drawn between the flexible fingers 158, 160, the surgeon may use a grasper or other surgical instrument to engage the manipulation formation 166 formed on the endless collar member 154 to position and or retain the device 150 in a desired orientation.

Figure 22:
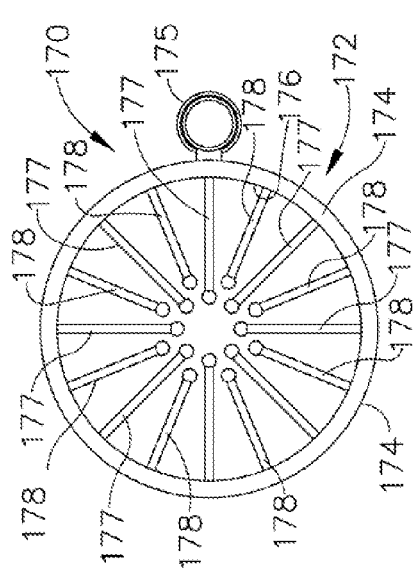
FIG. 22 is a top view of another bowel retractor device embodiment of the present invention.
Figure 23:
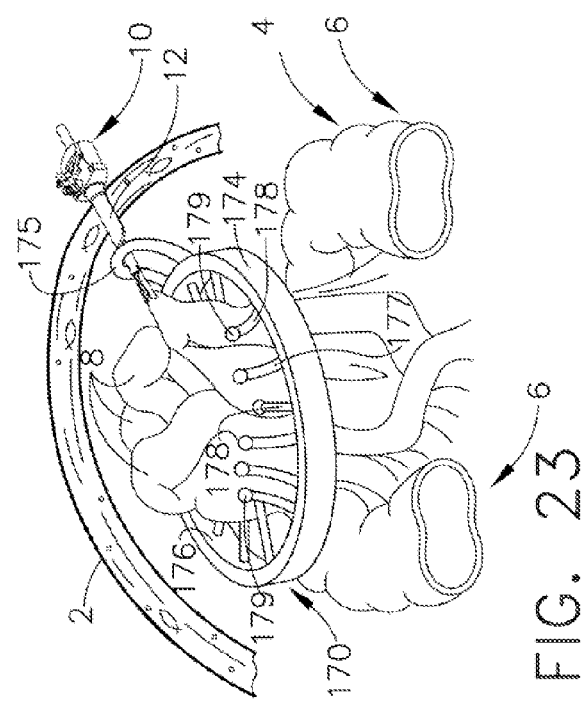
FIG. 23 is a perspective view of the bowel retractor device embodiment of FIG. 22 inside a portion of a patient's abdomen and supporting a non-target bowel portion therein.

FIG. 22 illustrates another bowel retractor device embodiment 170 of the present invention. The bowel retractor device 170 includes a body portion 172 that comprises a flexible endless collar member 174 that defines an inner area 176. In various embodiments, the flexible endless collar member 174 is elongated and is sized to be passed down through a trocar cannula 12 or other opening through the abdominal wall 2. The flexible end less collar member 174 may be fabricated from, for example, Santoprene, polypropylene, etc. The device 170 further includes a plurality of flexible fingers 177, 178 that protrude inwardly from the endless collar member 174. In at least one embodiment, the flexible fingers 178 extend between fingers 177. The flexible fingers 178 have a length that is shorter than the length of fingers 177. Also in various embodiments, each of the fingers 177, 178 have a ball-shaped member 179 formed on the end thereof. In at least one embodiment, the fingers 177, 178 lie along a common plane. Also in one embodiment, a manipulation formation 175 is formed on the endless collar member 174 to enable the device 170 to be easily manipulated with a surgical instrument such as a grasping instrument.

The bowel retractor device 170 may be used as follows. After the device 170 has been inserted through the trocar 10 or otherwise located at the surgical site, the surgeon may use graspers or other surgical instruments to draw the non-target portions 8 of the patient's bowel 4 through the central area 176. Once the non-target bowel portions 8 have been drawn between the flexible fingers 177, 178, the surgeon may use a grasper or other surgical instrument to engage the manipulation formation 175 formed on the endless collar member 174 to position and or retain the device 170 in a desired orientation.

Figure 27:
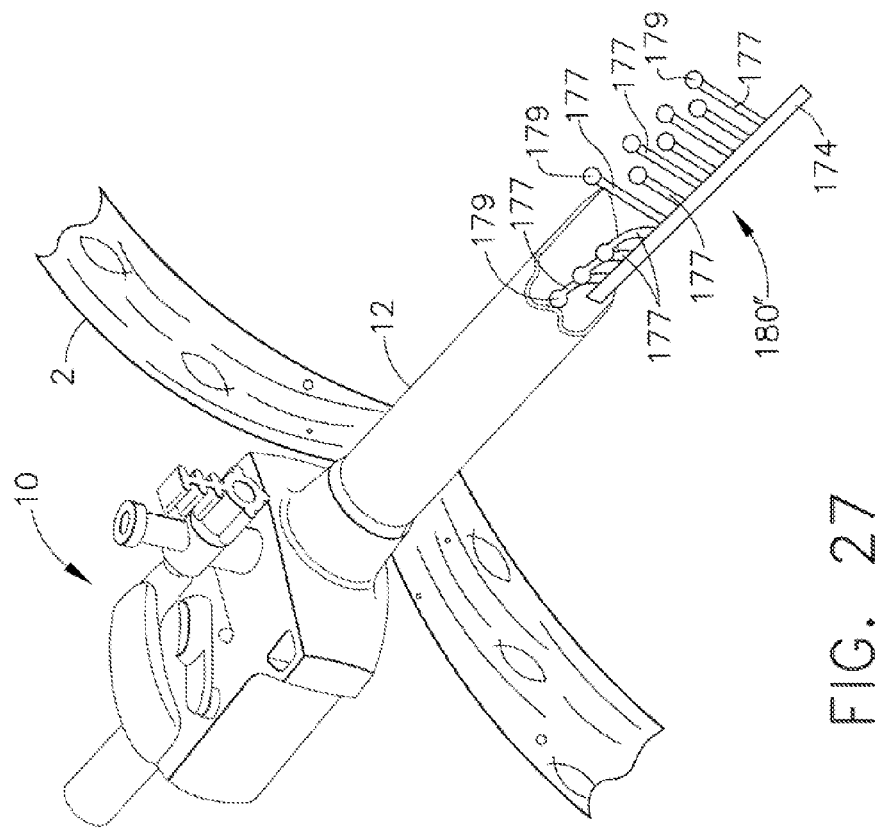
FIG. 27 is a perspective view of a trocar device inserted through the abdominal wall of a patient with a bowel retractor device embodiment being passed through the trocar cannula.
Figure 24:
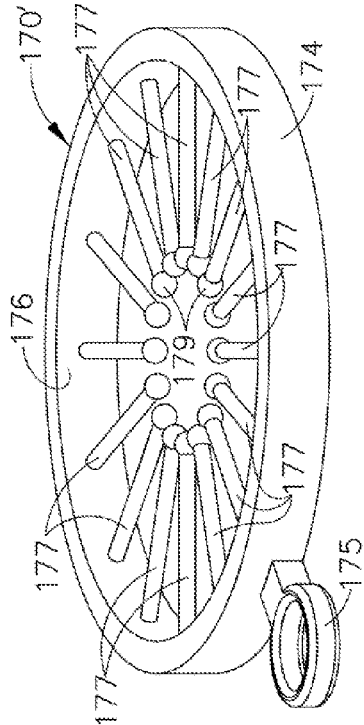
FIG. 24 is a perspective view of another bowel retractor device embodiment of the present invention.
Figure 25:
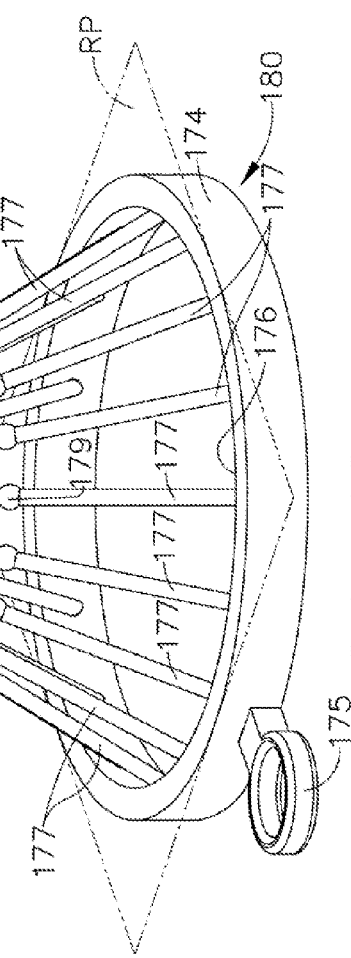
FIG. 25 is a perspective view of another bowel retractor device embodiment of the present invention.
Figure 26:
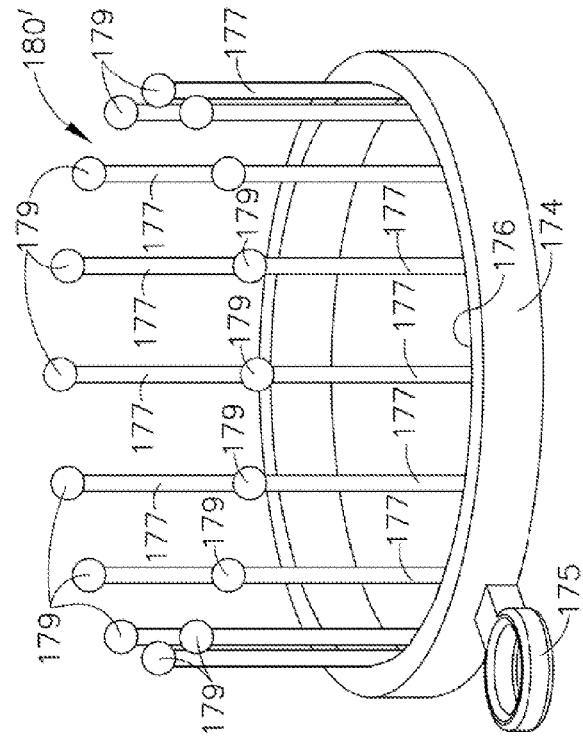
FIG. 26 is a perspective view of another bowel retractor device embodiment of the present invention.

FIG. 24 illustrates a bowel retractor device 170' that is substantially identical in construction and use as bowel retractor device 170 except that device 170' only has fingers 177 that all have a common length. FIG. 25 illustrates a bowel retractor device 180 that is substantially identical in construction and use as bowel retractor device 170', except that fingers 177 protrude out of the inner area 176. In particular, the endless collar 174 defines a reference plane "RP" and each of the fingers 177 extend transversely to reference plane RP. The bowel retractor device embodiment 180 depicted in FIG. 25 is substantially identical to bowel retractor device 170', except that fingers 177 all taper away from the endless collar 174 in a general frusto-conical configuration. That is, each of the fingers 177 extend along an axes that will ultimately intersect at a common point. The bowel retractor device 180' in FIG. 26 is substantially identical in construction and use as bowel retractor device 180 except that the fingers 177 extend out of the open area such that they are substantially perpendicular to the reference plane RP and are substantially parallel to each other. The bowel retractor device 180" in FIG. 27 is substantially identical to the bowel retractor device 180' except that the fingers 177 have different lengths. The bowel retractor devices 170', 180, 180', 180" may all be used in the various manners described above.

Figure 28:
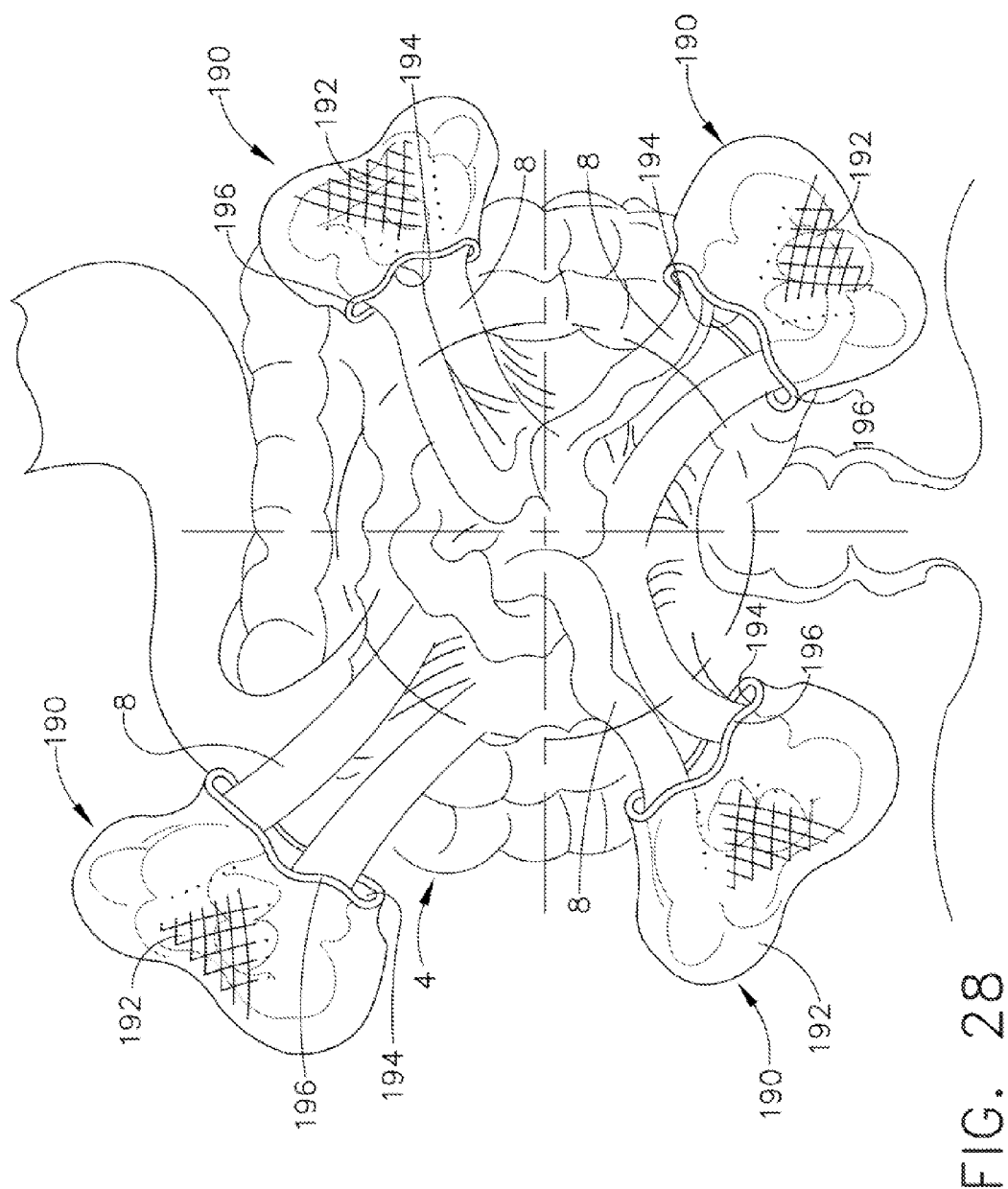
FIG. 28 is a perspective view of a portion of a patient's colon with four bowel retractor device embodiments of the present invention supporting non-target bowel portions.

FIG. 28 illustrates the use of four bowel retractor devices 190 for supporting the non-target bowel portions 8 in each of four quadrants involved in the surgical procedure. In at least one embodiment, each bowel retractor device 190 comprises a flexible pouch 192 that has an opening 194 therein. In one embodiment, the opening is surrounded by a collar member 196 in the form of an elastic band. The pouches 192 may be rolled up into a first collapsed position to enable them to be inserted through a trocar cannula 12. Once the pouches 192 have been inserted into the surgical area, the surgeon may open each pouch 192 and install it over a portion of non-target bowel 8. Once the pouches have been installed over the various non-target bowel portion(s) 8, they may be separated into quadrants which provide the surgeon with physical and visual access to the target bowel portion. Those of ordinary skill of the art will understand that various numbers of pouches 192 may be employed as needed.

Figure 29:
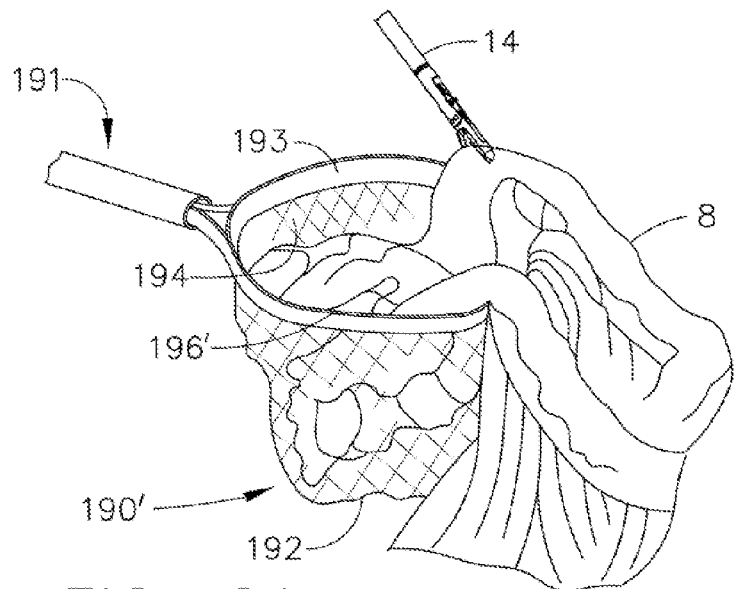
FIG. 29 is a partial perspective view of another bowel retractor device embodiment of the present invention being supported in an expanded position by an installation tool embodiment of the present invention.
Figure 30:
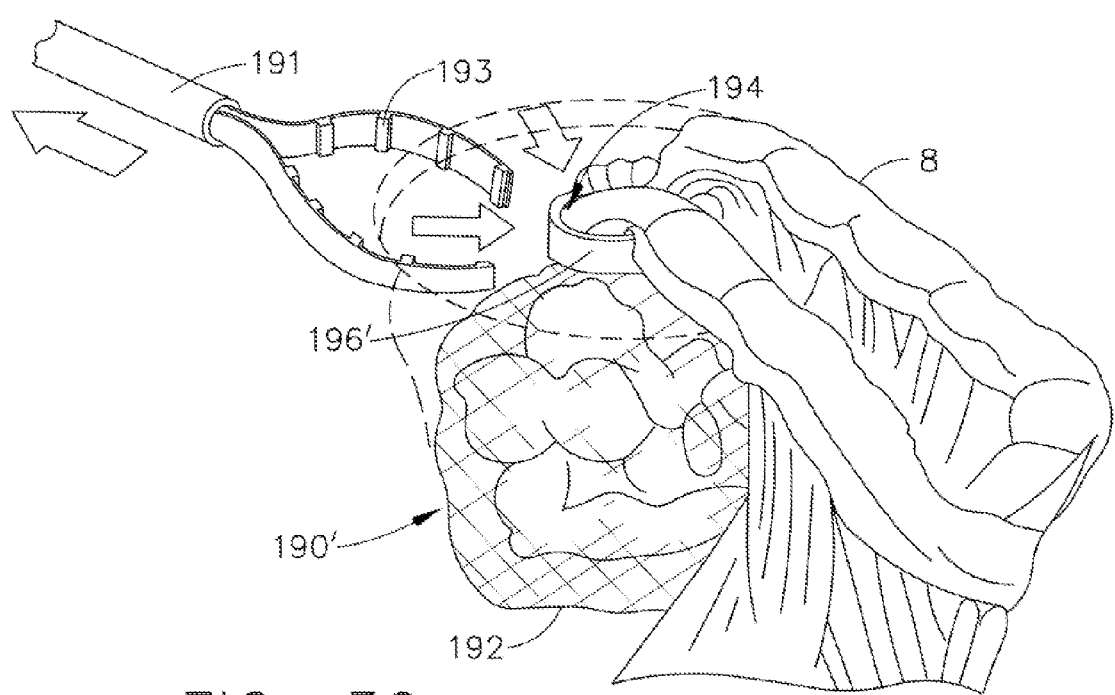
FIG. 30 is another perspective view of the bowel retractor device embodiment of FIG. 29 supporting a bowel portion therein with the installation tool removed therefrom.

FIGS. 29 and 30 illustrate another bowel retractor device 190' that is substantially identical to bowel retractor device 190, except that the collar member comprises an elastic band 196' that may be expanded from a non-expanded or collapsed state to an expanded state by inserting a selectively expandable and contractible installation head 193 of an installation tool 191 into the opening 194. When the installation head 193 is expanded, the elastic collar or band 196' is retained in the expanded state to permit the non-target bowel portions 8 to be inserted into the pouch 192 through the opening 194. Once the non-target bowel portion 8 has been inserted into the pouch, the installation head 193 is moved to the contracted position and removed from the elastic collar 196' which lightly contracts around the non-target bowel portions 8 protruding through the opening 194 to retain the non-target bowel portion 8 within the pouch 192 without damaging the non-target bowel portion 8 protruding therefrom.

Figure 31:
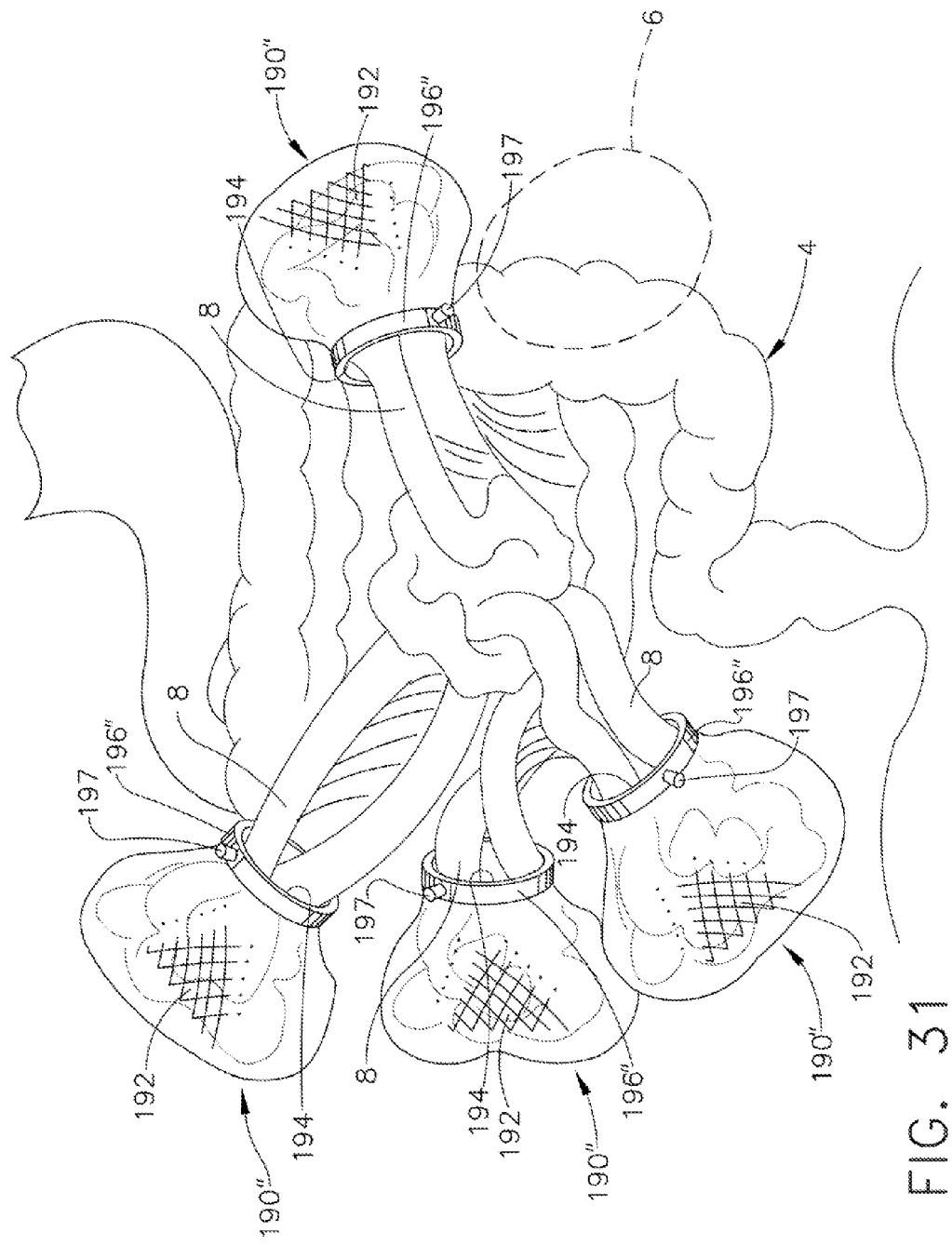
FIG. 31 is a perspective view of a portion of a patient's colon with four other bowel retractor device embodiments of the present invention supporting non-target bowel portions.

The bowel retractor device 190" in FIG. 31 is substantially identical in construction and use as bowel retractor device 190 except that the collar 196" is a cinchable member. For example, the collar 196" may comprise an expandable belt-type member that may be expanded to form a desired opening and then locked in position by a lock screw 197. Thus, the surgeon may release the lock screw 197 to enable the opening to be expanded for installation over a portion of the non-target bowel portion 8 and thereafter cinched in and locked with locking screw 197 to retain the pouch 192 on the non-target bowel portion 8 captured therein.

Figure 36:
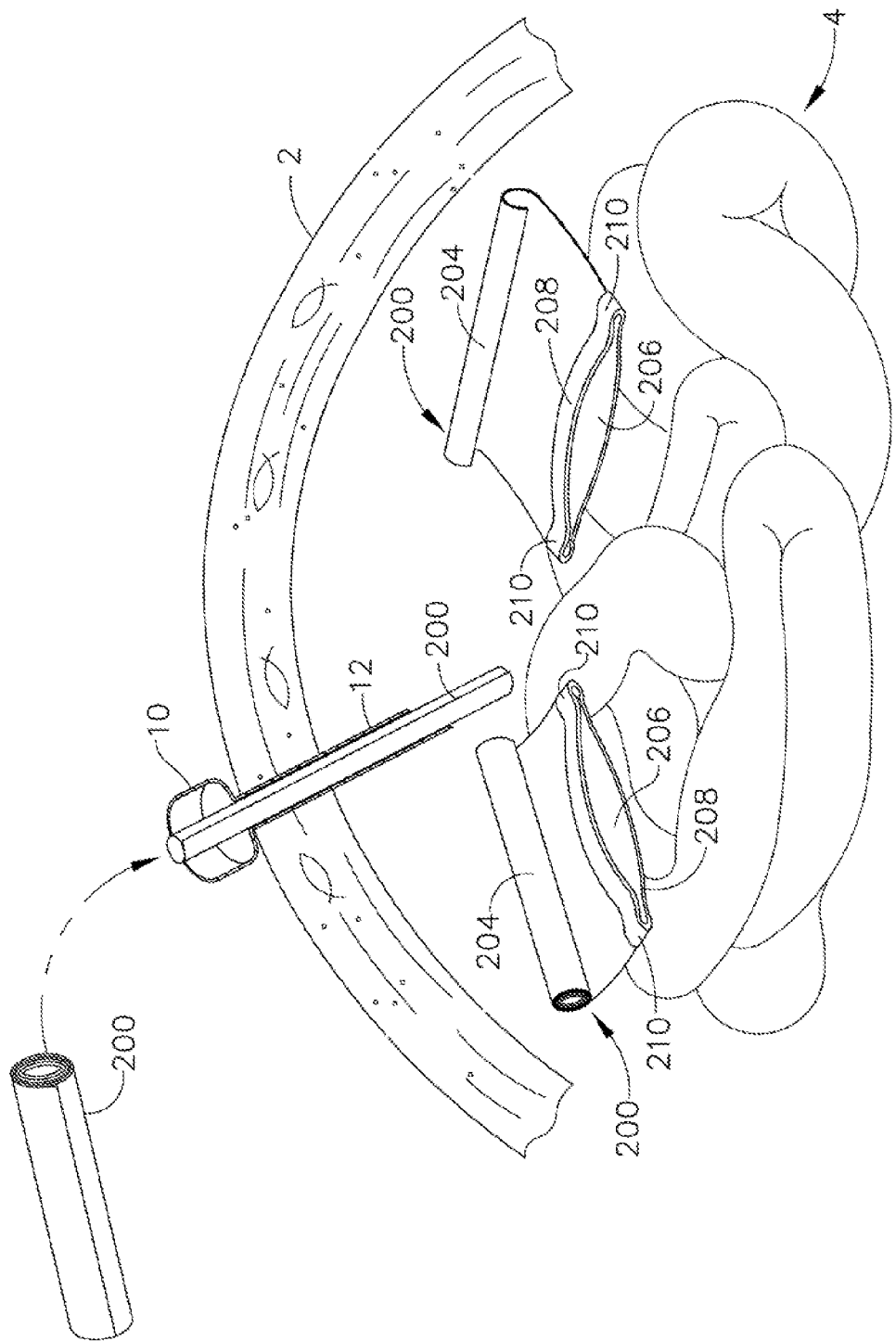
FIG. 36 is a perspective view of three bowel retractor device embodiments of FIGS. 32-35 inside a portion of a patient's abdomen.
Figure 37:
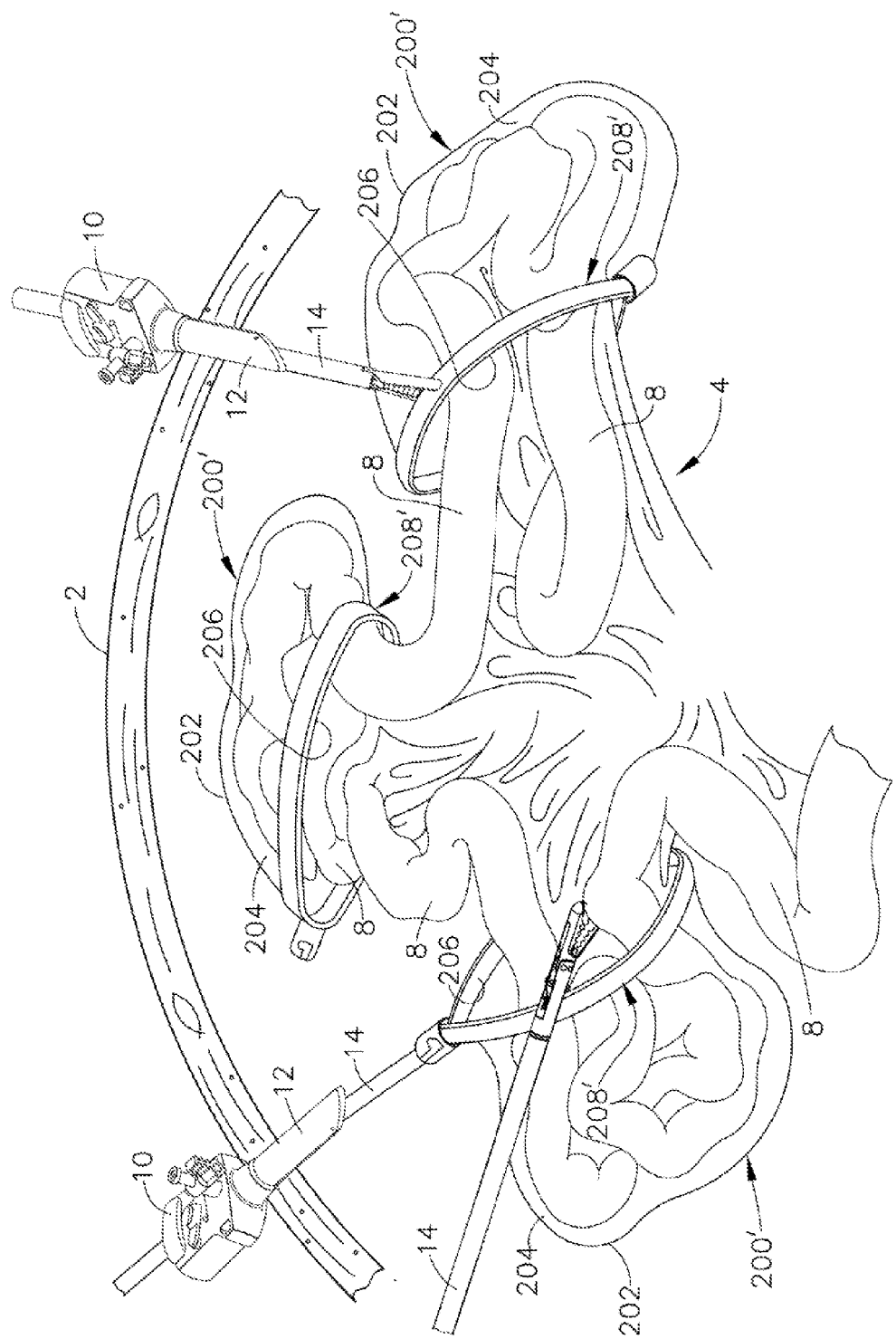
FIG. 37 is a perspective view of a patient's abdomen and bowel retractor device embodiments of the present invention supporting portions of the patient's bowel therein.
Figure 38:
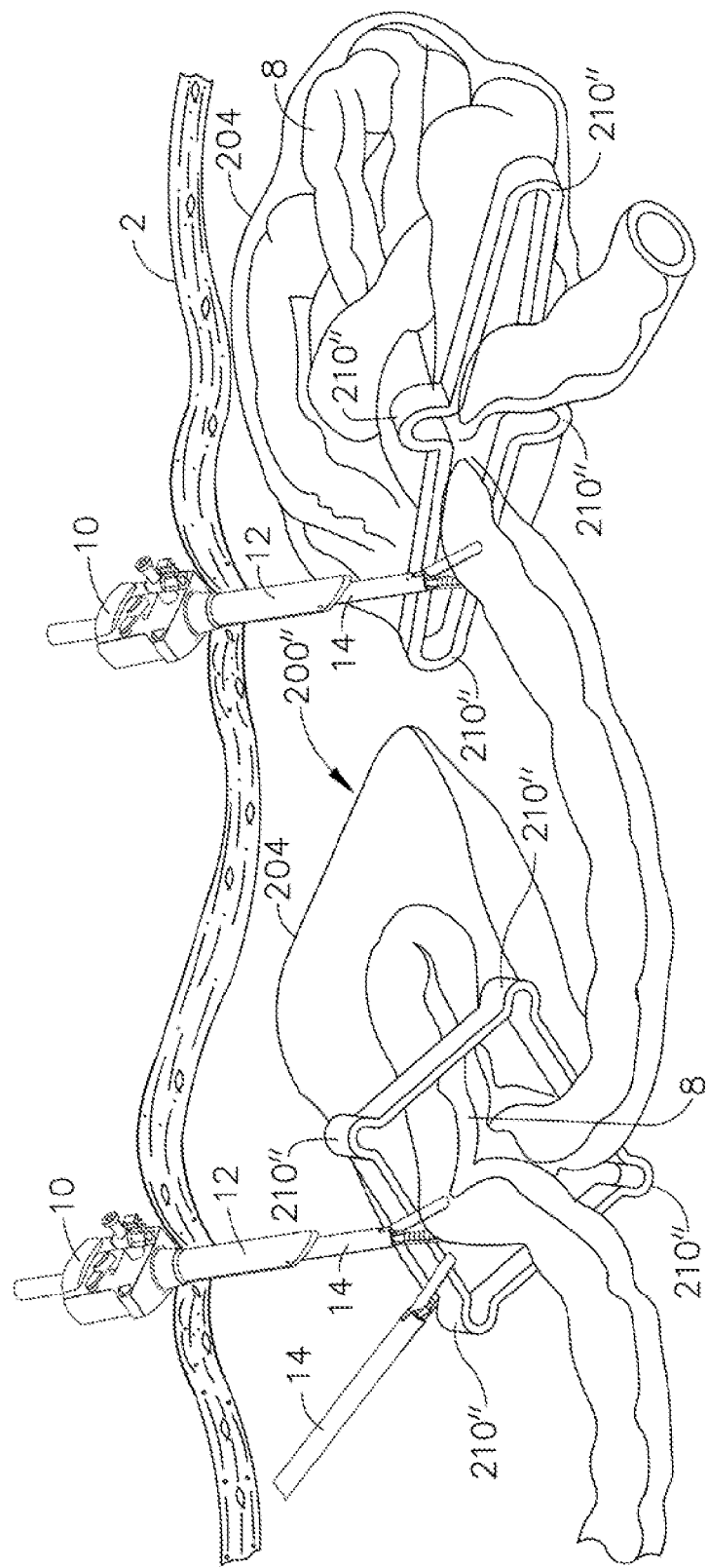
FIG. 38 is a perspective view of a patient's abdomen and bowel retractor device embodiments of the present invention supporting portions of the patient's bowel therein.
Figure 39:
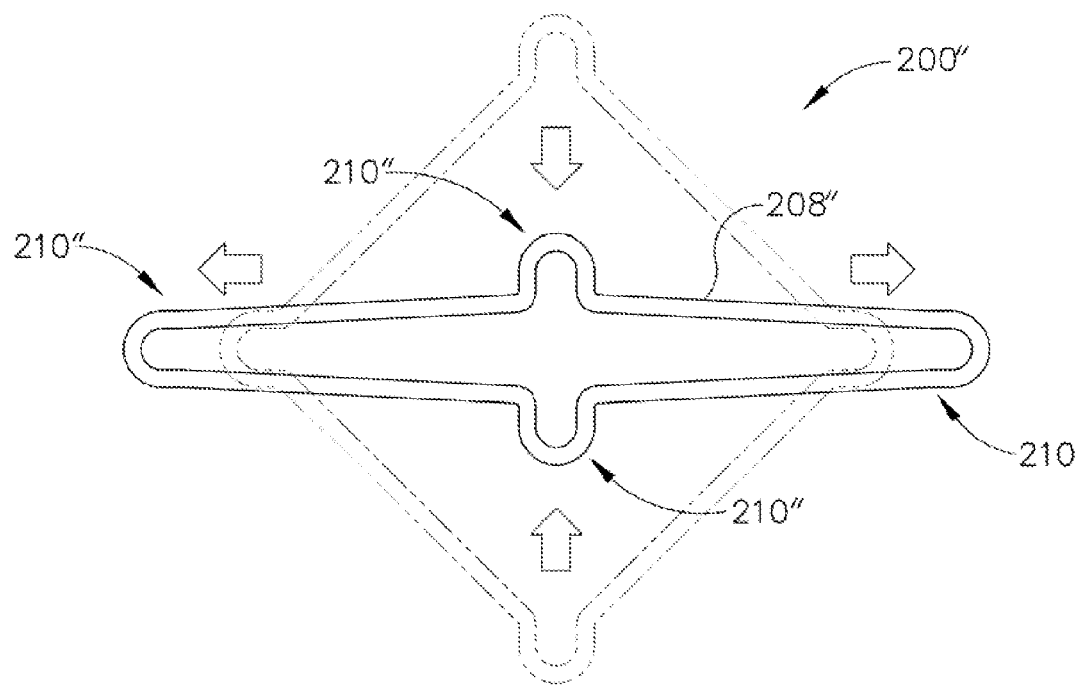
FIG. 39 is a top view of one of the bowel retractor devices depicted in FIG. 38 in a closed position.
Figure 40:
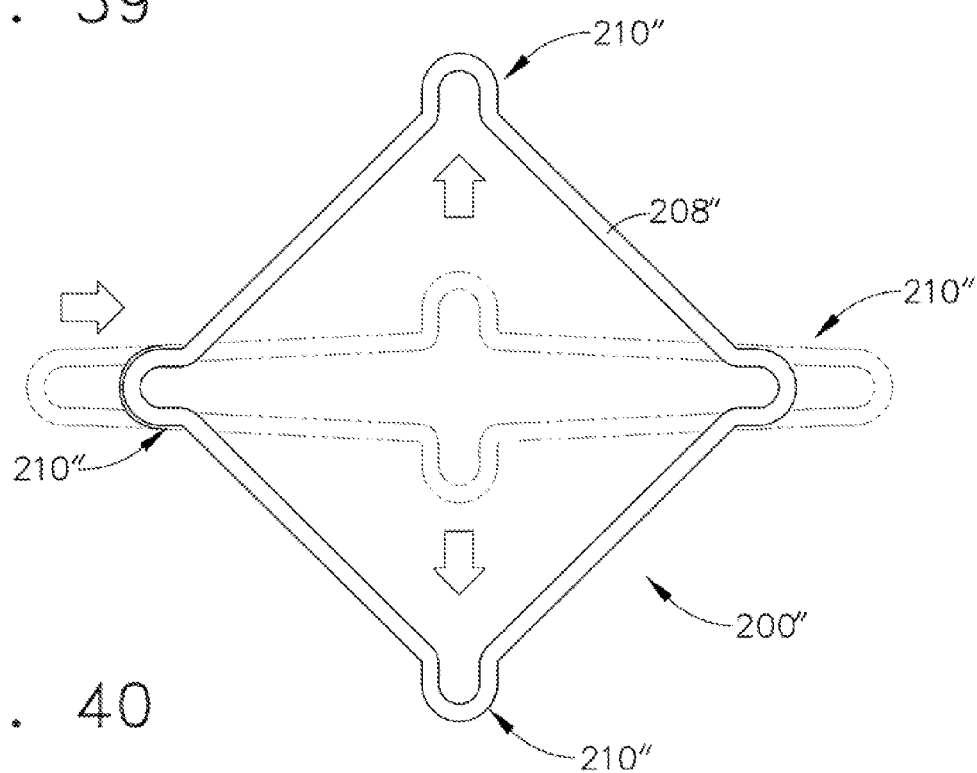
FIG. 40 is another top view of the bowel retractor device of FIGS. 38 and 39 in an open position.

FIGS. 32-36 illustrate another form of bowel retractor device 200 embodiment of the present invention. In various forms, the bowel retractor device 200 comprises a body portion 202 in the form of a pouch 204. In various embodiments, the pouch 204 may have a cinchable opening 206 therein. In at least one embodiment, a closure member 208 is attached to the pouch 204 such that it extends around the opening 206. The closure member 208 may be configured with two diametrically opposed hinge portions 210 that facilitates movement of the closure member 208 from a collapsed or closed position (FIG. 33) to an open position (FIG. 32). As illustrated in FIG. 32, the closure member 208 may be moved to the open position by applying opposing forces "F1" on the hinge portions 210 as well as applying opening forces "F2" in opposite directions to the closure member 208. The bowel retractor device 200 may be inserted into the patient through a trocar 10 as shown in FIG. 34. To facilitate insertion of the retractor device 200 through the trocar cannula 12, the device 200 may be rolled up as shown in FIGS. 34-36. FIG. 37 illustrates another bowel retractor device 200' that is substantially identical in construction and use as bowel retractor device 200 except that the closure member 208' is substantially spring-loaded. Such spring loading may be created by the configuration of the closure member itself or be assisted with one or more spring members (not shown) embedded therein. FIGS. 38-40 illustrate another bowel retractor embodiment 200" that is essentially the same as the bowel retractor 200, except that the closure member 208" has four hinge portions 210".

The closure members 208, 208', 208" of the bowel retractor devices 200, 200', 210", respectively are designed in their normal state to be biased to a closed position or state. When in the closed state, however, the closure members 208, 208', 208" may be designed to limit the closure force exerted onto the portion of the bowel received therein to minimize the risk of occlusion of blood flow to the captured bowel portion as well as to allow peristalsis to continue. Such closure bias is designed to immediately immobilize the non-target portions 8 of the bowel placed in the pouch so that it does not slip back out. The hinge portions 210, 210', 210" enable the closure members 208, 208', 210" to be forced open for the entire loading period, or more preferably, the closure member could be opened only as bowel segments are pulled in. The closure portions then maintain the opening in a closed position while the surgeon moves to grasp the next section of bowel to be introduced into the pouch. Thus, use of the biased closed temporary bowel retractor devices 200, 200', 200" improve the ease of introducing bowel portions therein as the closure portions thereof can automatically close itself to keep the non-target bowel portion from slipping back out of the pouch. The maximum cinching load also prevents inadvertent damage to the non-target bowel during retraction. In use, the surgeon may insert several of the devices 200, 200', and/or 200" through a trocar, trocars or other openings in the patient at the beginning of the surgical procedure. Lengths of the non-target bowel portions 8 would be placed into a pouch and then when the pouch became sufficiently full, the closure member thereof would be "snapped" shut. This procedure may be repeated with other bowel retractor devices 200, 200', 200" as needed. These loaded pouches could then be easily moved from one position to another in the abdomen cavity during the procedure. The surgeon is able to easily grasp and move en masse sections of the bowel 4 to move it out of the way. Additionally, the pouches could be temporarily clipped or pinned to different abdomen wall structures to facilitate more retraction. Also, the various pouch-type bowel retractor devices disclosed above may include a grasper access hole through the bottom of the pouch to enable a grasper instrument to be inserted therethrough and out through the pouch opening to grasp bowel portions to draw them into the pouch. Such arrangement serves to facilitate easy introduction of the bowel portions into the pouch. The hinge arrangements also serve to bias the closure members closed around the bowel portions as they are drawn into the pouch.

Figure 42:
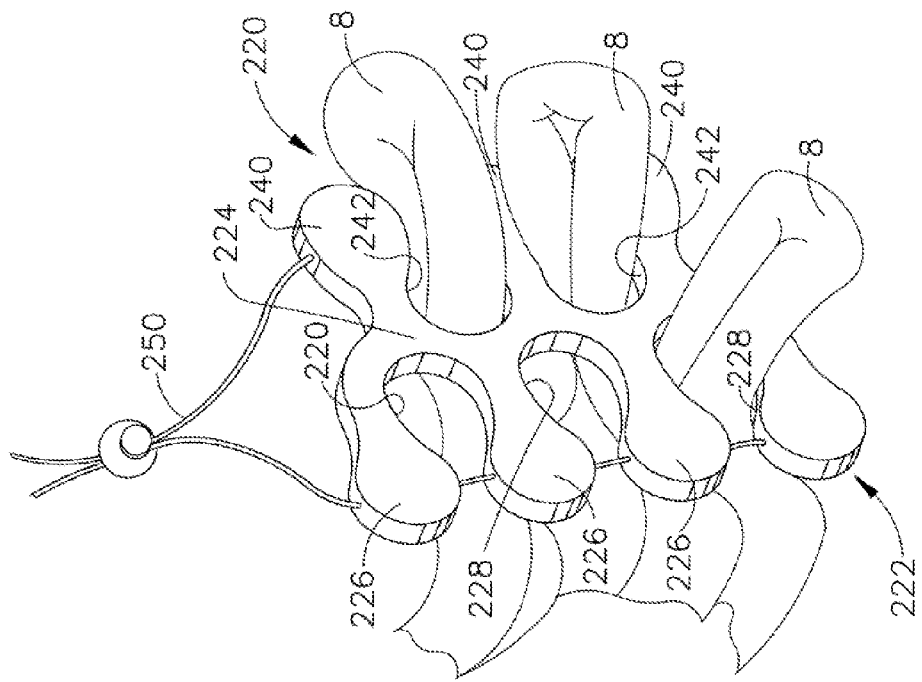
FIG. 42 is a partial perspective view of another bowel retractor device embodiment of the present invention supporting a portion of a patient's bowel therein.
Figure 41:
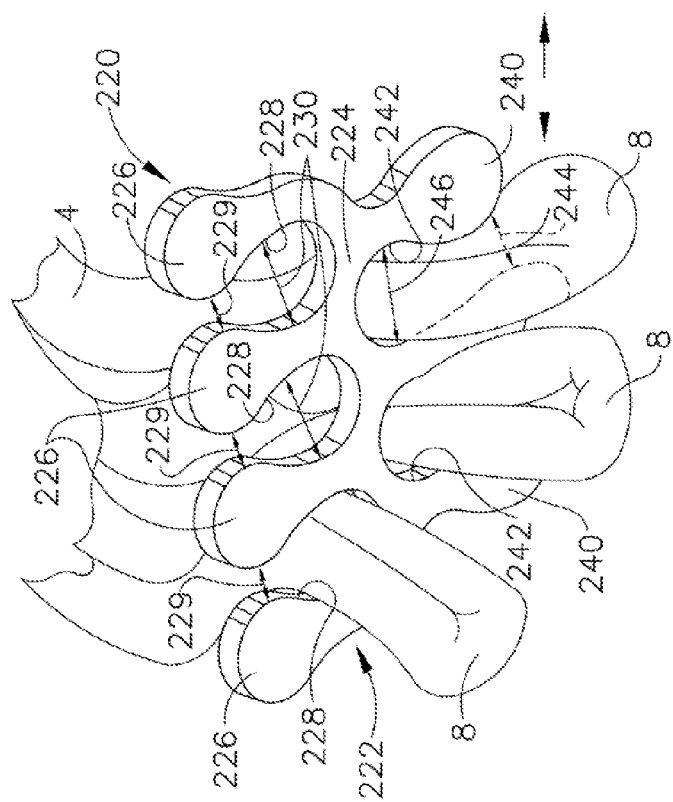
FIG. 41 is a partial perspective view of another bowel retractor device embodiment of the present invention supporting a portion of a patient's bowel therein.

FIGS. 41 and 42 illustrate another bowel retractor device embodiment 220 of the present invention. Various embodiments include a substantially elastic body portion 222 that is insertable through an opening in a patient's body to a second expanded position wherein a portion of the patient's bowel may be supported thereby. In various embodiments, the body portion 222 includes a central portion 224 that has at least three flexible first arms 226 that protrude from the central portion 224 in a first direction. A first opening 228 is formed between each first arm 226. In at least one embodiment, each first opening has a shape that generally resembles a portion of an hourglass. In particular, each first opening 228 has a first neck portion 229 that is narrower than a first bottom portion 230. As can be further seen in FIGS. 41 and 42, the bowel retractor device 220 further comprises at least two flexible second arms 240 that protrude from a second side of the central portion 224 in a second direction. In one embodiment, each second arm 240 protrudes from the center portion 224 at positions opposite to the first opening 228. In other embodiments, the second arms 240 may be aligned with corresponding first arms 226. A second opening 242 is formed between each second arm 240. In at least one embodiment, each second opening 242 has a shape that generally resembles a portion of an hourglass. In particular, each second opening 242 has a second neck portion 244 that is narrower than a second bottom portion 246. In other embodiments, the first and second openings may be provided in other shapes.

Various embodiments of the bowel retractor device 220 are fabricated from a foam material or other elastic material. In other embodiments, each of the first and second arms 226, 240 have a bendable wire member or wire members (nitinal, spring steel, etc.) embedded therein to enable the arms 226, 240 to be advantageously bent in position to facilitate insertion of the retractor device 220 through a trocar or other opening. In still other embodiments, the center portion 224 may have a bendable wire portion therein. In other arrangements, bendable wires may be embedded in the center portion 224 and each of the first and second arms 226, 240. In other embodiments, at least one bendable wire is embedded in at least one of the center portion 224, a first arm 226 and/or a second arm 240. Such arrangements facilitate the bending of the device 220 in a position that facilitates its insertion through a trocar cannula. In other embodiments, however, the device 220 may be sized such that it can pass through a trocar cannula without having to be bent or collapsed.

In use, once the bowel retractor device 220 has been inserted into the patient through a trocar or other opening in the patient's body, the surgeon may grasp the retractor 220 with a grasping instrument and then pull non-target bowel portions 8 through the first and/or second openings 228, 242. The bowel portions 8 may be held in place by manipulating the formable arms 226, 240. In various embodiments, a suture drawstring 250 (FIG. 42) is provided to further support and tie down the retractors position. This step could be repeated several times creating a grouped clump of small bowel that can be moved around merely by moving the bowel retractor 220. Various embodiments of the retractor 220 can be bent into whatever restraining form would be most useful to keep the clump out of the working space. It could be lodged up behind a trocar cannula 12 or held back with a grasping instrument 14, whatever is convenient for the specific case. The flexible fit holds the small bowel together without strangulating it or interfering with the peristalsis causing swelling. The fit is tight enough to prevent the bowel from slipping right back out.

FIGS. 43-46 illustrate another bowel retractor device embodiment 260 of the present invention. In various embodiments, the retractor 260 comprises an inflatable ring 262 that defines an interior area 264. The inwardly facing surface 266 of the inflatable ring 262 is textured with, for example, dimples 269, etc. The ring 262 is supplied with a pressurized medium such as, for example, through a supply conduit 270 that is attached to a source of pressurized medium 272 located outside of the patient's body. See FIG. 45.

Figure 46:
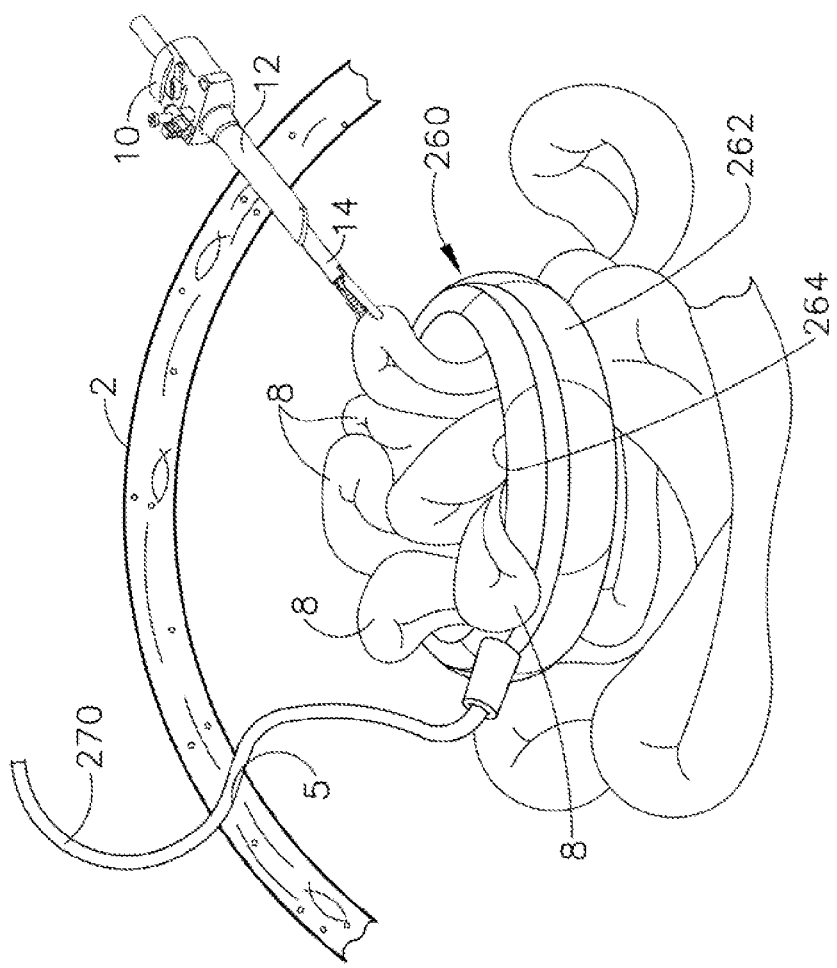
FIG. 46 is another partial perspective view of a portion of a patient's abdomen containing the bowel retractor device embodiment of FIG. 44 therein and supporting a portion of the patient's bowel therein.
Figure 44:
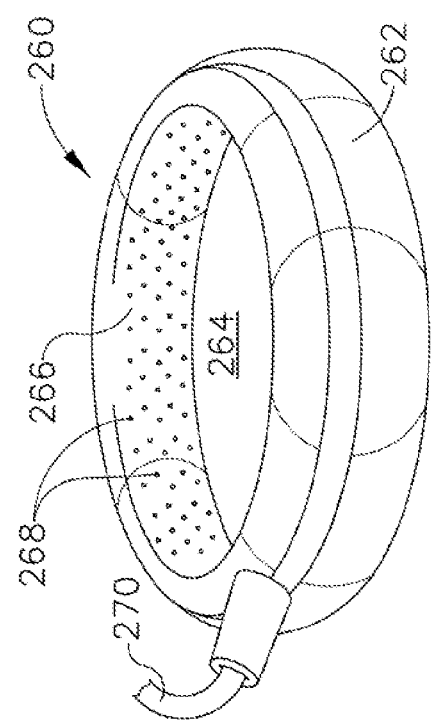
FIG. 44 is another perspective view of the portion of bowel retractor device embodiment of FIG. 43 in an inflated state.

To use the bowel retractor device 260, the retractor 262 (in its collapsed or uninflated state) as well as the supply conduit may be inserted through a trocar 10 mounted in the abdominal wall 2 or it may be inserted into the surgical site through another opening 5 in the abdominal wall 2 as shown in FIG. 46. Once in position, the surgeon may then grasp non-target bowel portions 8 with one or more grasping instruments 14 to pull the non-target bowel portions 8 through the interior area 264. The surgeon may first inflate the ring 262 prior to pulling the non-target bowel portions 8 through the interior area 264 or the surgeon may pull the non-target bowel portions 8 through the interior area 264 prior to inflating the ring 262. Once inflated, the textured surface 266 retains the bowel portions in position. One or more retractors 260 may be used in the various methods described above to advantageously provide the surgeon with physical and visual access to the target tissue during the operation.

The various bowel retraction devices disclosed herein represent vast improvements over other retraction devices and methods commonly employed with performing operations on a patient's bowel. Many embodiments may be easily inserted into the patient through a common trocar cannula. The devices are easily manipulatable with common grasping instruments. Several of such devices may be used as necessary to advantageously locate non-target portion(s) of bowel in a desired position to provide the surgeon with physical and visual access to the target tissue. Once bunches of bowel have been gathered together, the bunches may be easily moved and positioned en masse to a desired location. The retractors may be easily clipped to portions of the abdomen to hold the retractor in position if necessary. While the various retractor devices disclosed herein have been described in detail for use in connection with bowel surgeries, it is conceivable that various embodiments of the present invention could also be employed to retract other forms of tissue/organs without departing from the spirit and scope of the present invention.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. A bowel retractor device comprising:
    a flexible outer collar formed from a substantially flexible planar film material including a central opening therethrough, said film material further including a plurality of outwardly protruding tabs that are radially spaced around said central opening and wherein each said tab has at least one opening therethrough, said flexible outer collar being configurable from a first collapsed position wherein said flexible outer collar is configured to be fully passed through an opening in a patient's body and a second expanded position wherein a portion of the patient's bowel may be pulled through the central opening in a desired orientation; and
    a flexible member radially woven through the tabs such that the flexible member extends around the central opening and being separately cinchable relative thereto.

2. The bowel refractor of claim 1 wherein said flexible member comprises a flexible cable.

3. A bowel refractor device comprising a flexible annular ring defining a central area; and
    a plurality of transversely overlapping interwoven members extending across said central area, each said interwoven member having two ends non-removably affixed to said flexible annular ring, said interwoven members having a weave tightness that permits at least one portion of a patient's bowel to be pulled between at least some adjacent said interwoven members and retained therebetween without injuring the at least one bowel portion and wherein the retractor device is configurable from a first collapsed position wherein said annular ring is configured to be fully passed through an opening in a patient's body as a unit and a second expanded position.

4. The bowel retractor device of claim 3 wherein said plurality of interwoven flexible members comprises a plurality of interwoven flexible ribbon members.

5. The bowel retractor device of claim 3 wherein said plurality of interwoven flexible members comprises:
    a first layer of interwoven members; and
    a second layer of interwoven members spaced from said first layer of interwoven members.

6. The bowel retractor device of claim 5 wherein each said interwoven member has a substantially circular cross-sectional shape.

* * * * *